US008846861B2

(12) United States Patent
Davis et al.

(10) Patent No.: US 8,846,861 B2
(45) Date of Patent: Sep. 30, 2014

(54) PEPTIDE CLEARING AGENTS

(75) Inventors: Paul James Davis, Felmersham (GB); James Alexander Schouten, Beds (GB)

(73) Assignee: Mologic Ltd (GB)

( * ) Notice: Subject to any disclaimer, the term of this patent is extended or adjusted under 35 U.S.C. 154(b) by 35 days.

(21) Appl. No.: 13/497,967

(22) PCT Filed: Sep. 23, 2010

(86) PCT No.: PCT/GB2010/001796
§ 371 (c)(1),
(2), (4) Date: Nov. 14, 2012

(87) PCT Pub. No.: WO2011/036457
PCT Pub. Date: Mar. 31, 2011

(65) Prior Publication Data
US 2013/0053543 A1     Feb. 28, 2013

(30) Foreign Application Priority Data

Sep. 23, 2009  (GB) .................................. 0916749.5

(51) Int. Cl.
| A61K 38/14 | (2006.01) |
| C07K 9/00 | (2006.01) |
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |
| A61K 38/04 | (2006.01) |
| C07K 5/02 | (2006.01) |
| B82Y 5/00 | (2011.01) |
| A61K 47/48 | (2006.01) |

(52) U.S. Cl.
CPC ......... *A61K 47/48353* (2013.01); *C07K 5/0202* (2013.01); *B82Y 5/00* (2013.01); *A61K 47/48092* (2013.01)
USPC ............................ 530/322; 530/324; 530/330

(58) Field of Classification Search
None
See application file for complete search history.

(56) References Cited

U.S. PATENT DOCUMENTS

| 5,958,408 | A | 9/1999 | Griffiths et al. |
| 6,075,010 | A | 6/2000 | Theodore et al. |
| 6,172,045 | B1 | 1/2001 | Theodore et al. |
| 2003/0068322 | A1 | 4/2003 | Hansen |
| 2003/0073157 | A1* | 4/2003 | Bertozzi et al. .............. 435/68.1 |
| 2006/0140858 | A1 | 6/2006 | Goldenberg et al. |

FOREIGN PATENT DOCUMENTS

| EP | 0308208 A1 | 3/1989 |
| EP | 2050761 A1 | 4/2009 |
| WO | WO-91/17761 A1 | 11/1991 |
| WO | WO-96/40245 A1 | 12/1996 |
| WO | WO-97/20580 A1 | 6/1997 |
| WO | WO-98/24478 A2 | 6/1998 |

OTHER PUBLICATIONS

Bagshawe, Antibody directed enzyme prodrug therapy (ADEPT), Annals of Oncology 5: 879-891, 1994.*
Leveille-Webster, Use of an Asialoglycoprotein Receptor—Targeted Magnetic Resonance Contrast Agent to Study Changes in Receptor Biology During Liver Regeneration and Endotoxemia in Rats, Hepatology 23:1631-1641, 1996.*
Huang, PP2243, PubMed Accession No. AAQ15261.*
Takada, Rapid High-Affinity Transport of a Chemotherapeutic Amino Acid across the Blood-Brain Barrier, Cancer Research 52: 2191-2196, 1992.*
Mizuno et al. Synthesis of a Glycopeptide Containing Oligosaccharides: Chemoenzymatic Syntehsis of Eel Calcitonin Analogues Having Natural N-Linked oligosaccharides. JACS 1999, vol. 121, pp. 284-290.*
Buskas et al. Glycopeptides as versatile tools for glycobiology. Glycobiology, 2006. vol. 16, No. 8, pp. 113R-136R.*
Bagshawe, K.D. "Targeting: The ADEPT Story So Far," Current Drug Targets, 10: 152-157 (2009).
Evans, Karen A., et al.; "Amino acid anthranilamide derivatives as a new class of glycogen phosphorylase inhibitors," Bioorganic & Medicinal Chemistry Letters 18: 4068-4071 (2008).
Napier, M.P., et al.; "Antibody-directed Enzyme Prodrug Therapy: Efficacy and Mechanism of Action in Colorectal Carcinoma[1]," Clinical Cancer Research, 6: 765-772 (2000).
International Search Report for PCT/GB2010/001796 mailed Dec. 17, 2010.
International Search Report for GB0916749.5 dated Jan. 21, 2010.
Khan, Tariq H., et al. "Novel Inhibitors of Carboxypeptidase $G_2$ ($CPG_2$): Potential Use in Antibody-Directed Enzyme Prodrug Therapy," J. Med. Chem. 42(6): 951-956 (1999).
Meijer, Dirk K.F., et al. "Targeting of Drugs to the Liver," Seminars in Liver Disease; 15(3): 202-256 (1995).
Polt, Robin, et al. "Practical glycopeptide analgesics: Blood-brain barrier transport and binding of glycosylated enkephalin analogs," Peptides for the New Millennium. Proceedings of the American Peptide Symposium, No. 16th, pp. 770-772 (Jun. 26, 1999).
EP Application No. 10 757 623.3 Examination Report dated Nov. 25, 2013.

* cited by examiner

*Primary Examiner* — Marcela M Cordero Garcia
(74) *Attorney, Agent, or Firm* — Foley Hoag LLP

(57) ABSTRACT

A peptide clearing agent is provided for clearance of a conjugate of an enzyme and a binding molecule which binds specifically at a target location from a non-target location in a subject. The peptide clearing agent binds the active site of the enzyme. The peptide also binds to the asialoglycoprotein receptor expressed by hepatic cells to facilitate clearance through the liver. The peptide may be glycosylated to facilitate clearance through the liver by binding to hepatic cells expressing an asialoglycoprotein receptor. Typically, the peptide prevents or inhibits enzyme activity upon binding to the enzyme and is not substantially modified by the enzyme activity. The peptide may be based upon the dipeptide aminonaphthoic acid (ANA)-glutamate (Glu) and may comprise the amino acid sequence serine (Ser)-Alanine (Ala)-aminonaphthoic acid (ANA)-glutamate (Glu). In such cases, the enzyme of interest is typically CPG2.

28 Claims, 21 Drawing Sheets

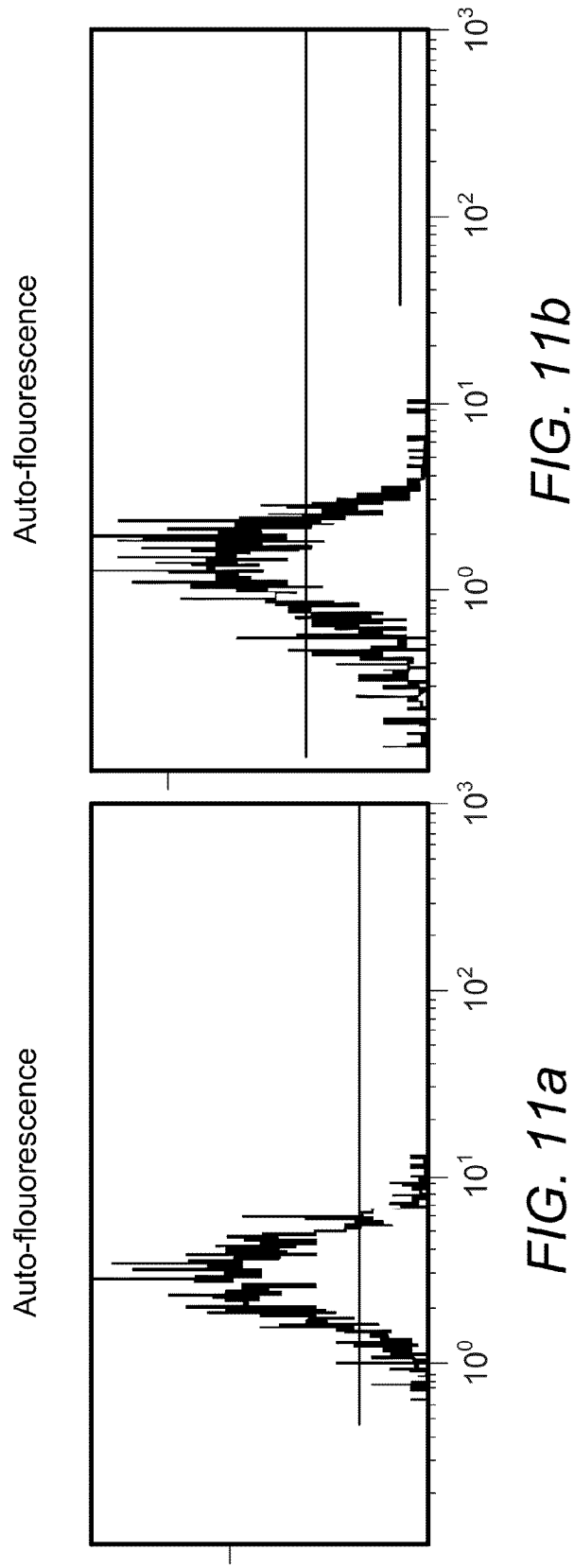

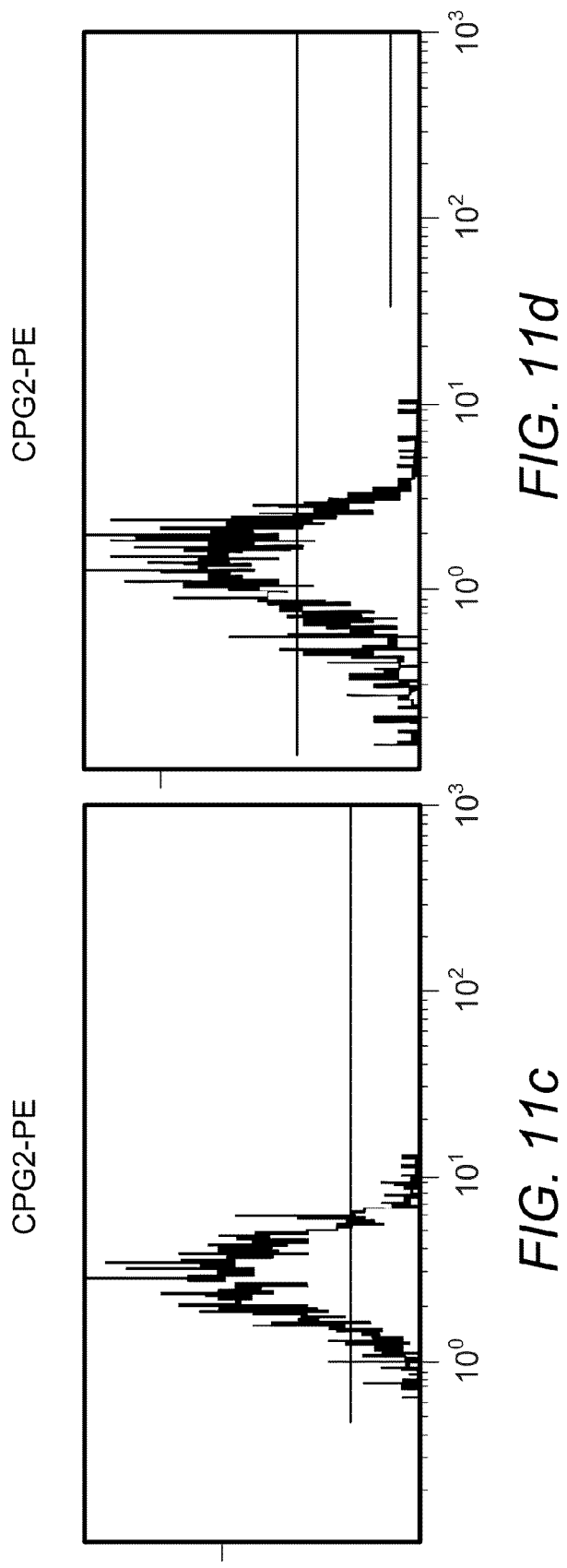

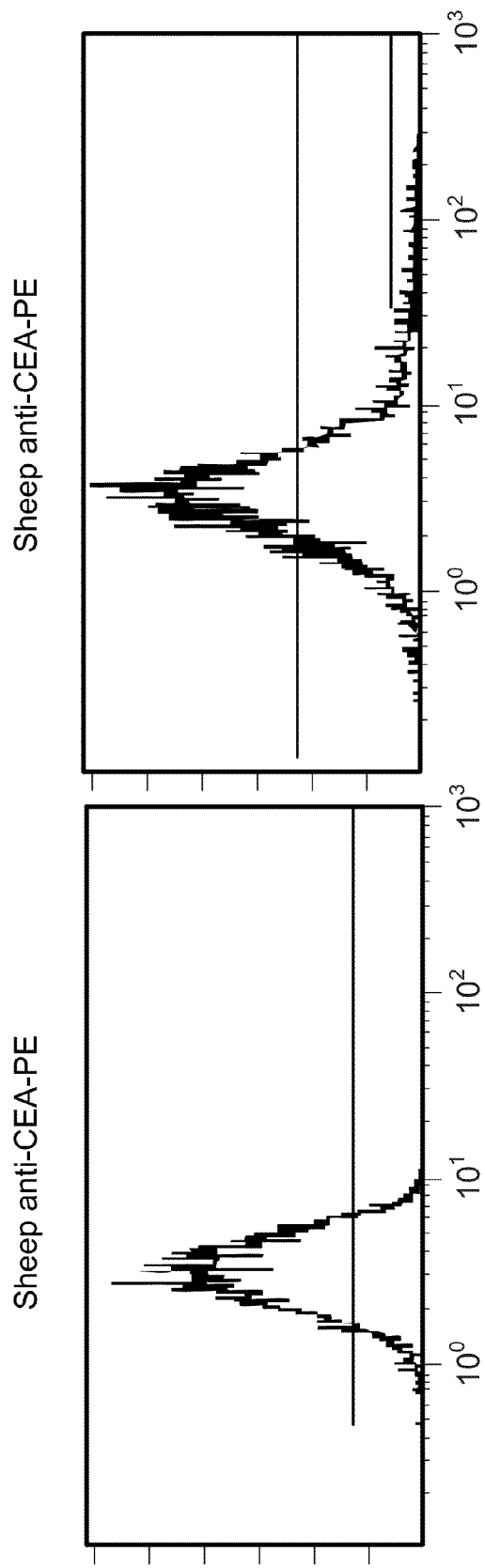

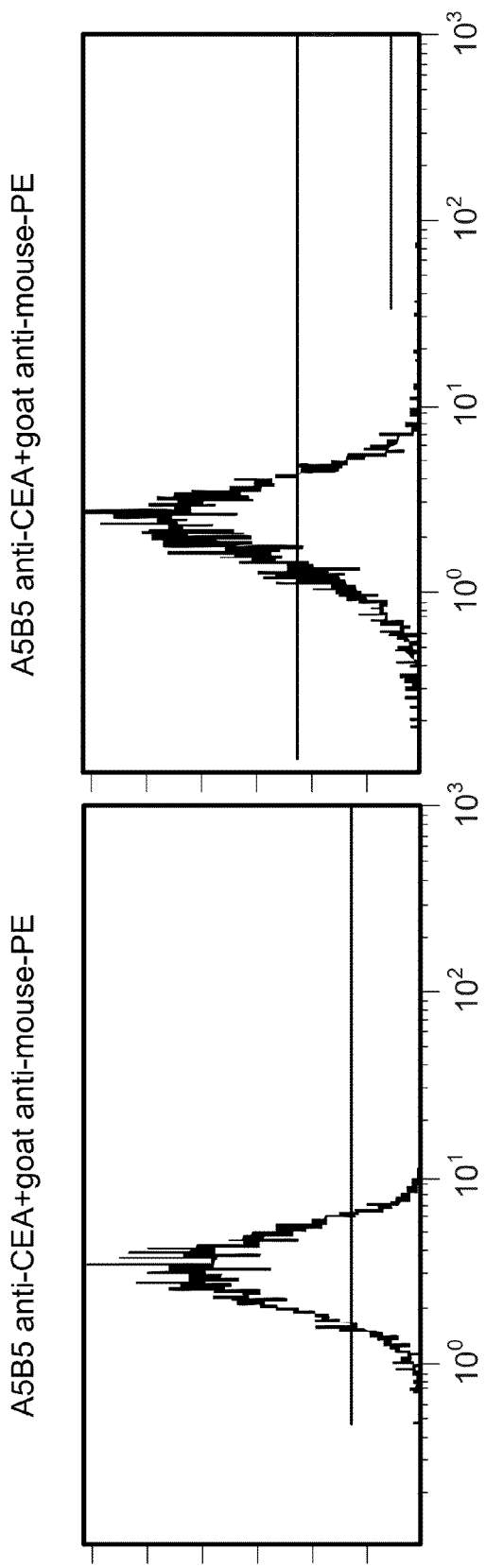

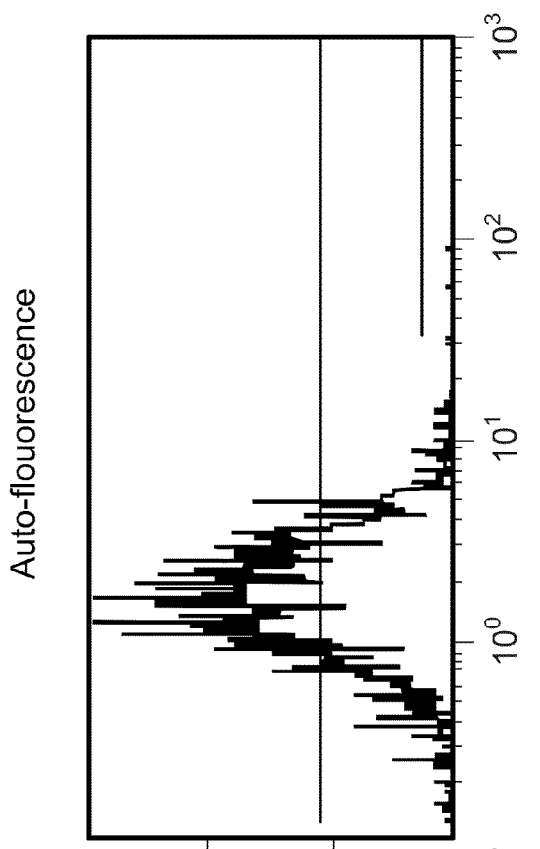
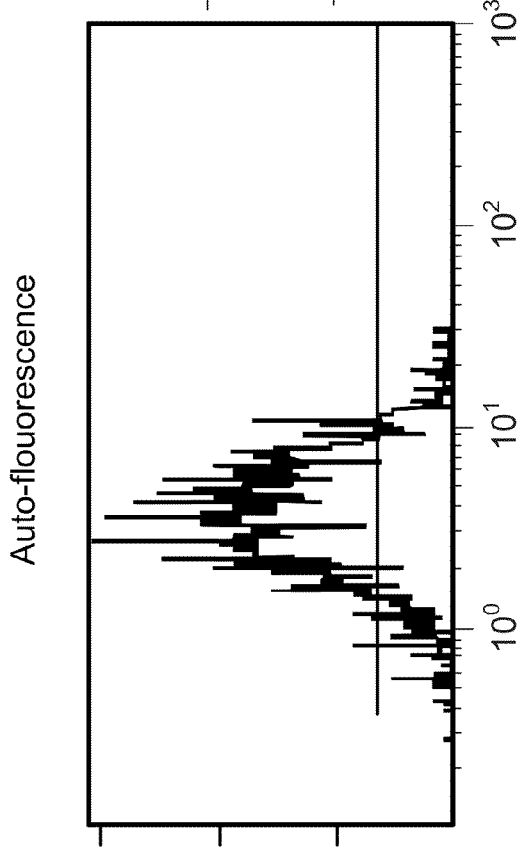
FIG. 12b
FIG. 12a

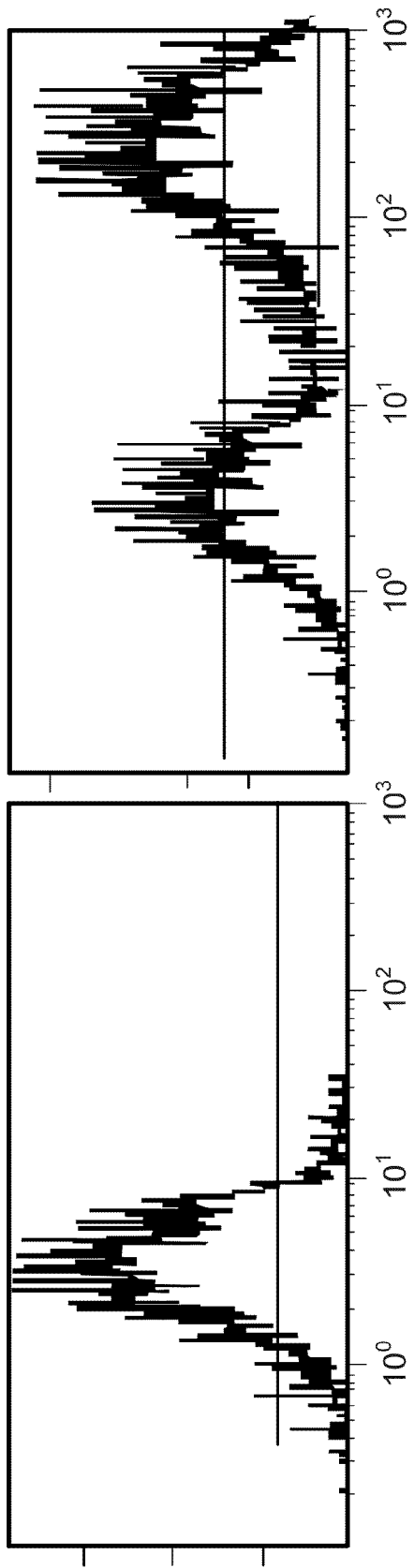

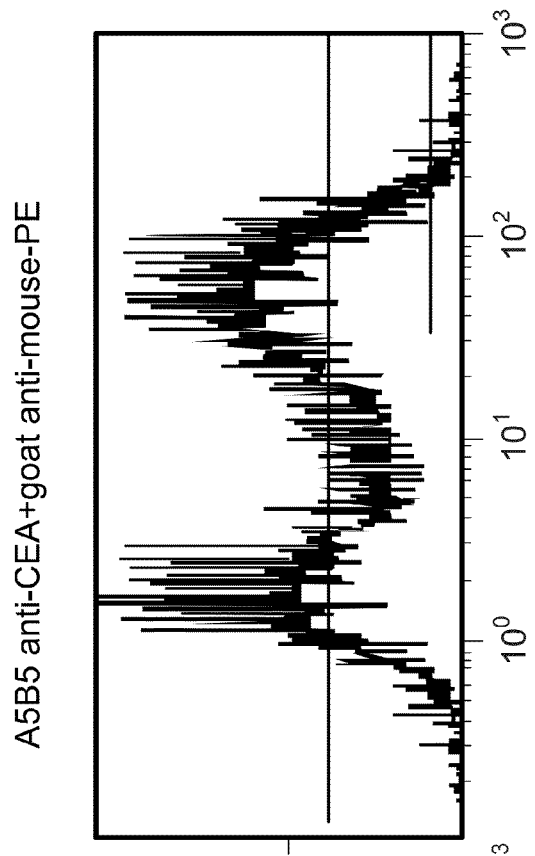
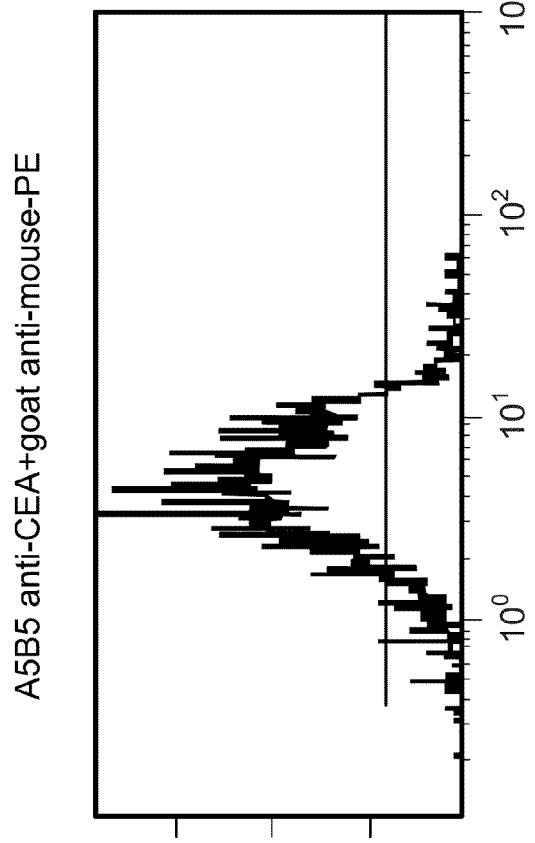
FIG. 12j
FIG. 12i

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial sequence
```

```
<220> FEATURE:
<223> OTHER INFORMATION: synthesised peptide
<220> FEATURE:
<221> NAME/KEY: S
<222> LOCATION: (1)..(1)
<223> OTHER INFORMATION: S may be glycosylated
<220> FEATURE:
<221> NAME/KEY: X
<222> LOCATION: (3)..(3)
<223> OTHER INFORMATION: X = amino-naphthoic acid

<400> SEQUENCE: 1

Ser Ala Xaa Glu
1
```

PEPTIDE CLEARING AGENTS

This application is a 371 national stage application of PCT/GB2010/001796, filed Sep. 23, 2010, which claims priority to GB 0916749.5, filed Sep. 23, 2009. The entire contents of each of these applications are hereby incorporated by reference.

SEQUENCE LISTING

The instant application contains a Sequence Listing which has been submitted via EFS-Web and is hereby incorporated by reference in its entirety. Said ASCII copy, created on Apr. 19, 2012, is named ISA__22901.txt and is 569 bytes in size.

FIELD OF THE INVENTION

The invention relates to peptide clearing agents which act to clear an enzyme from a non-target location in a subject. The invention also relates to methods of producing these peptide clearing agents.

BACKGROUND OF THE INVENTION

Antibody directed enzyme prodrug therapy (ADEPT) aims to improve the selectivity of cytotoxic drugs. An enzyme is employed which acts to convert a prodrug to an active drug. The action of the drug is localised to the site of interest through use of an antibody which binds to a tumour associated antigen. This antibody is conjugated to, or formed as a fusion protein with, the enzyme which acts on the prodrug thus ensuring prodrug conversion occurs predominantly at the site of interest.

The therapeutic efficiency and specificity of ADEPT systems have, however, been limited by conversion of prodrug in normal tissues, due to residual enzyme-antibody conjugate and leakage of the conjugate from the tumour (which can be due to loss of the antigen from the tumour cells into the circulation). In an attempt to address this issue, an enzyme clearance stage has been developed to remove residual enzyme activity and thus minimize side-effects of the therapy. This has relied upon a further antibody that binds to the enzyme. This antibody is glycosylated to facilitate clearance via the liver (1).

US 2003-0068322 (Hansen) describes antibody based clearing agents to effect clearance of circulating targeting protein-enzyme conjugate. In one embodiment, the clearing agent binds to the enzyme. However, the clearing agent binds at a site that does not interfere with enzyme activity. WO 96/40245 and U.S. Pat. No. 5,958,408 represent similar disclosures.

Napier et al—Clinical Cancer Research Vol. 6, 765 to 772, March 2000—describes a clinical trial in which ten patients with colorectal carcinoma expressing carcinoembryonic antigen received antibody-directed enzyme pro drug therapy with A5B7 F(ab')2 antibody to carcinoembryonic antigen conjugated to carboxypeptidase G2 (CPG2). In this trial, a galactosylated antibody directed against the active site of CPG2 (SB43-gal) was given to clear and inactivate circulating enzyme. Napier states that a human anti-mouse antibody response (HAMA) was found in all patients after two weeks preventing further therapy (see page 768 second column under the heading immune response). Napier suggest that immunosuppressive agents may be utilised in order to facilitate the use of such clearing agents in the context of ADEPT therapy.

WO 91/17761 describes a technique distinct from the ADEPT technique. In this technique, an antagonist is targeted to normal cells to enable the cytotoxin to be used therapeutically to treat only the diseased cells. Thus, the method aims to protect normal cells.

EP0308208 relates to antibodies and antibody conjugates modified by conjugation to glycoside residues that bind to the human hepatic asialoglycoprotein receptor to enable rapid clearance from the circulation.

EP0733072 and U.S. Pat. No. 5,876,691 describe antibodies specific for carcinoembryonic antigen (CEA).

DESCRIPTION OF THE INVENTION

The use of a glycosylated second or further antibody as a clearing agent is associated with several problems, the most important of which are as follows:—

1) The second (clearing) antibody is inevitably immunogenic, so limiting its use to a few repeat cycles of use.

2) It has a high affinity for the enzyme, which is difficult to modulate. High affinity means that it may well also bind too strongly to enzyme localized at the target location, thus limiting effectiveness of local drug generation.

3) Its high molecular weight means that a large mass of glycoprotein has to be inoculated in order to bind and clear the fusion protein 4) Cost, production and regulatory issues of a second antibody component are relatively difficult.

For these reasons, a new kind of clearing agent is desired. Thus, the invention provides a peptide clearing agent for clearance of a conjugate of an enzyme and a binding molecule which binds specifically at a target location, from a non-target location in a subject through binding of the peptide to the conjugate, wherein the peptide binds to the asialoglycoprotein receptor expressed by hepatic cells. This leads to internalisation of the conjugate found at a non-target location. Thus, binding of the peptide to the asialoglycoprotein receptor expressed by hepatic cells facilitates clearance of the peptide. In specific embodiments, the peptide is glycosylated to facilitate clearance through the liver by binding to hepatic cells expressing an asialoglycoprotein receptor. More specifically, the invention provides a peptide clearing agent for clearance of a conjugate of an enzyme and a binding molecule which binds specifically at a target location, from a non-target location in a subject through binding of the peptide to the active site of the enzyme, wherein the peptide (clearing agent also) binds to the asialoglycoprotein receptor expressed by hepatic cells. This leads to internalisation of the conjugate found at a non-target location. Thus, binding of the peptide to the asialoglycoprotein receptor expressed by hepatic cells facilitates clearance of the peptide. In specific embodiments, the peptide is glycosylated to facilitate clearance through the liver by binding to hepatic cells expressing an asialoglycoprotein receptor.

The subject is typically a human or animal and is preferably a human. Clearance is thus generally from the circulation via the liver. The peptide clearing agent of the invention binds to the asialoglycoprotein receptor expressed by hepatic cells, leading to internalisation of the conjugate found at a non-target location.

The clearing agent of the invention solves the problems associated with an antibody based clearing agent for the following reasons:—

1) It is of low molecular weight so that it is non-immunogenic

2) Its affinity for the enzyme binding site can be tuned by undertaking positional substitutions with alternative amino acids until the required affinity of binding is achieved.

3) Its low molecular weight also means that a given clearance efficiency can be achieved with a much lower mass than that of the fusion protein.
4) It may be produced as a synthetic chemical by known chemical procedures, thus the peptide clearing agent has fewer problems of cost, production efficiency and regulatory barriers.

As mentioned above, ADEPT systems rely upon localisation of enzyme activity through an antibody, or other binding molecule, which binds to a target location in the subject, such as a tumour associated antigen. ADEPT systems consist of several molecular modules which co-operate together to deliver a large but highly localised dose of a drug, such as a cytotoxic agent, to cells that are diseased (e.g. cancer cells) or that are causing disease (e.g. parasitic cells).

The peptide clearing agent of the invention binds to a conjugate of an enzyme and a binding molecule, more specifically to the enzyme and in particular the active site of the enzyme. The binding molecule may be any molecule that is capable of binding to a target location and thus localising the enzyme to that particular location. In certain embodiments, the enzyme is concentrated at a target location through specific binding of the binding molecule at the target location. Thus, the binding molecule may bind to a receptor or antigen or other molecule expressed by a cell in the subject, in particular stably expressed on the cell surface. Preferably, although not exclusively, the binding molecule comprises, consists essentially of or consists of an antibody or antigen-binding derivative thereof. Any suitable antibody may be utilised, although IgG immunoglobulins are most typically employed. Heavy chain antibodies and humanized forms of non-human antibodies are, of course, included within the scope of the term "antibody". Antibodies may be polyclonal although monoclonal antibodies are generally preferred. Antigen-binding derivatives cover all fragments of antibodies and other derivatives that retain the ability to specifically bind to the target of interest. Monovalent fragments are often employed. Examples include Fab fragments, scFv, single domain antibodies, nanobodies, minibodies, diabodies, triabodies etc.

The binding molecule binds specifically at the target location to avoid unwanted binding to non-target locations, such as cells that do not express the particular antigen. It should also have a high affinity, sufficient to achieve rapid uptake at the target location. However, binding affinity is such that the binding molecule can fully access the target location—taking the example of binding to a tumour associated antigen, the binding molecule must not bind so tightly that it can bind only to the periphery of any tumour mass. In practice any selective binding capability is sufficient to provide a focussed therapeutic action, and the required minimum efficiency will vary from application to application. The binding affinity of the binding molecule is preferably associated with a low dissociation constant (i.e. slow off-rate) to minimise leakage of the molecule from the target location to which it has bound. Thus, binding affinity and kinetics are balanced as far as possible to secure a targeted and effective action at the target location.

The enzyme is conjugated with the binding molecule in a manner such that the enzyme is delivered to the target location by virtue of its association with the binding molecule. Typically, the enzyme is covalently linked to the binding molecule so that everywhere a binding agent molecule binds, at least one enzyme molecule is bound, too. Thus, the binding characteristics considered above actually apply to a hybrid molecule, in the form of a binding molecule-enzyme chemical conjugate or a binding molecule-enzyme fusion protein derived from a single gene expressing both molecules as a continuous amino-acid sequence, folded into appropriate functional domains. The enzyme acts to convert a pro-drug to an active drug at the target location. The enzyme is preferably one that is not naturally present in the subject to prevent undesired activity and side effects in the subject. The enzyme's role is to modify a prodrug molecule that is non-toxic until acted upon by the enzyme to release an active drug, generally a short lived active drug. Thus, the binding molecule based localisation of enzyme activity ensures that the prodrug is cleaved only in the immediate vicinity of the target location. In certain embodiments, the prodrug is a substance that when cleaved by the enzyme forms a highly toxic but short lived molecule—properties which ensure that it is potent but can only kill the cells that exist in the vicinity in which prodrug is cleaved. In specific embodiments, alkylating agents such as benzoic acid mustard derivatives are employed. Preferably, the action of the drug is concentration dependent. A terminal glutamate on an alkylating agent renders it inactive, thus making them ideal partners for use with CPG2, which acts to cleave this glutamate residue. A high concentration of drug generated at the target location could leak back into the blood and cause toxicity, so a short half life is an important attribute of the active drug.

Any suitable enzyme may be employed that permits conversion of inactive prodrug to active drug at the target location. Suitable enzymes already employed in the context of ADEPT systems include carboxypeptidase G2, alkaline phosphatase, beta-glucoronidase, penicillin-V-amidase, beta-lactamase, beta-glucosidase and nitroreductase. Potentially useful enzyme/pro-drug combinations, useful for generating peptide clearing agents of the invention are listed in table 1.

TABLE 1

Enzymes useful in the invention to design suitable peptide clearing agents (4)

| Enzyme | Prodrug | Drug |
|---|---|---|
| Carboxypeptidase G2 | Benzoic acid mustard glutamates | Benzoic acid mustards |
| Cytosine deaminase | 5-fluorocytosine | 5-fluorouracil |
| Carboxypeptidase A | Methotrexate-alanine | Methotrexate |
| Alpha-galactosidase | N-[4-(α-D-galactopyranosyl)-benzyloxycarbonyl]-daunorubicin | Daunorubicin |
| Beta-glucosidase | amygdalin | Cyanide |
| Beta-lactamase | Vinca-cephalosporin | 4-desacetylvinblastine-3-carboxyhydrazide |
|  | Phenylenediamine mustard-cephalosporin | Phenylenediamine mustard |
|  | Nitrogen-mustard-cephalosporin | Nitrogen-mustards |
| Alkaline phosphatase | Phenolmustard phosphate | Phenolmustard |
|  | Doxorubicin phosphate | Doxorubicin |
|  | Mitomycin phosphate | Mitomycin alcohol |
|  | Etopside phosphate | Etopside |
| Penicillin amidase | Palytoxin-4-hydroxyphenyl-acetamide | Palytoxin |
|  | Doxorubicin-phenoxyacetamide | Doxorubicin |
|  | Melphalan-phenoxyacetamide | Melphalan |
| Nitroreductase | CB1954 | 5-(aziridine-1-yl)-4-hydroxylamino-2-nitrobenzamide |

A particularly preferred enzyme in the context of the invention is carboxypeptidase G2 (CPG2). CPG2 is a bacterial peptidase (from *Psuedomonas*). It is a folate hydrolyzing enzyme, which hydrolyzes the C-terminal glutamate moiety from folic acid and its analogues, such as methotrexate. Homogenous CPG2 has a molecular mass of 83,000 (Gel filtration) but following SDS PAGE a molecular mass of 41,400 is obtained, showing the enzyme to be dimeric. It has two active sites in each functional, intact dimer, and it is dependent for its structure and function on zinc.

The conjugate of binding molecule and enzyme is generally produced either by genetic means or by chemical conjugation using one of the many known chemical cross-linking methods. The genetic means generally comprise splicing the respective genes together so that both the enzyme and binding molecule proteins are expressed as a single combined protein with both functions ("fusion protein"). It is important for the fusion protein not to be glycosylated because a glycosylated fusion protein starts clearing itself through the liver as soon as it is given, with the result that less enzyme is delivered to the tumour than with a non-glycosylated form.

In specific embodiments of the invention, the peptide clearing agent prevents or inhibits enzyme activity upon binding to the enzyme. Thus, preferably, the peptide is not modified by the enzyme activity. By "not modified" is meant that the peptide retains binding affinity for the enzyme to permit clearance; modification may occur provided affinity is not lost. Peptide binding to the active site is a more effective manner of clearing if the peptide is resistant to the activity of the enzyme. One manner in which the peptides of the invention may be resistant to enzyme activity is to incorporate one or more D-form amino acids. For example, inclusion of a D-amino acid glutamate in a peptide clearing agent designed to bind to the active site of CPG2 may act to prevent hydrolysis of the peptide bond at this amino acid.

The binding molecule-enzyme conjugate binds at a target location. This is typically a cell type of interest, such as a tumour cell, for example. Specific binding at the target location may be due to binding to an antigen specific for the cell type of interest. In specific embodiments, the target location is an antigen expressed by tumour cells. Thus, for example in the case of oncological applications, the antigen expression should ideally be specific for the cancer cells, to avoid the risk of attacking non-cancerous host cells. The antigen is preferably tumour-specific, although it may be tumour associated. In addition, the antigen should be stably expressed on the surface (membrane) of the cells of interest. However, transient expression prior to release or shedding is possible in the context of the invention. The antigen characterising the target location preferably is not rapidly internalised, either spontaneously or when it is bound by the binding molecule. The reason for this is that the prodrug is typically administered systemically and intracellular enzyme would not readily interact with a prodrug in the circulation. One specific example of a target location is cells expressing the antigen known as carcino-embryonic antigen (CEA). This antigen is expressed by a substantial proportion of colorectal carcinomas (CRC) and thus permits localised treatment of CRC. Antibodies and derivatives capable of binding CEA are known in the art, such as ScFv anti-CEA discussed herein, which may or may not be produced as a fusion protein with CPG2.

The peptide clearing agent of the invention binds to the asialoglycoprotein receptor expressed by hepatic cells. This leads to internalisation of the conjugate found at a non-target location. Thus, binding of the peptide to the asialoglycoprotein receptor expressed by hepatic cells facilitates clearance of the peptide. In specific embodiments, the peptide is glycosylated to facilitate clearance through the liver by binding to hepatic cells expressing an asialoglycoprotein receptor. Thus, the peptides comprise of an amino acid sequence that binds to the enzyme with a binding affinity that permits complexes to be formed in the circulation between the peptide clearing agent and the conjugate of binding molecule and enzyme with sufficient stability to reach the hepatic cells and to be taken up via the asialoglycoprotein receptor. However, the off rate of the peptide clearing agents must be sufficiently fast to allow dissociation from the conjugate of binding molecule and enzyme bound at the target location within the timescale of the dosing regime of the prodrug, otherwise prodrug to active drug conversion will be impeded. Thus, again there is a balance required between the affinity for asialoglycoprotein receptor expressed on hepatic cells on the one hand and the affinity of the peptide for the conjugate of binding molecule and enzyme on the other hand. In specific embodiments, the peptide has an affinity for the conjugate of binding molecule and enzyme, and in particular the (active site of the) enzyme, that is sufficient to permit clearance of the enzyme from the non-target location. In certain embodiments, the peptide (also) has a sufficiently rapid dissociation rate/high dissociation constant to not significantly affect enzyme activity at the target location. More specifically, the peptide's affinity for the conjugate of binding molecule and enzyme, and in particular the (active site of the) enzyme, may be around 10 fold (such as around 5 to around 15 fold, including all values inbetween) lower than the binding affinity of the binding molecule for its target location. Thus, binding of the conjugate of binding molecule and enzyme to the target location is favoured over clearance but the affinity of the peptide for the conjugate of binding molecule and enzyme, and in particular the (active site of the) enzyme, is still ample to secure efficient clearance of unbound conjugates via the liver, through internalisation following binding to the asialoglycoprotein receptor.

Peptide clearing agents of the invention are exemplified herein displaying appropriate kinetics and affinity properties. Such kinetic and affinity properties may be measured using any suitable means. Kinetic and affinity parameters may be derived based upon binding studies using Surface Plasmon Resonance (SPR), which is a well known technique (and commercially available, for example from GE Healthcare—Biacore system). Data obtained using a suitable instrument may be analysed by appropriate software to automatically derive the relevant parameters. An appropriate binding model may be applied by the software to ensure the fit to the curves is as close as possible. A chi2 value of less than 0.2 may be considered an acceptable fit.

In specific embodiments, the data may be obtained using commercially available Biaevaluation software using a single state binding model (1:1 Langmuir binding model). The peptide clearing agents of the invention may thus display on rates (association rate constants, Ka) of anywhere between around $1 \times 10^3$ $M^{-1}s^{-1}$ and $1 \times 10^7$ $M^{-1}s^{-1}$ in certain embodiments, or between around $1 \times 10^4$ $M^{-1}s^{-1}$ and $1 \times 10^6$ $M^{-1}s^{-1}$, or between around $1 \times 10^5$ $M^{-1}s^{-1}$ and $5 \times 10^5$ $M^{-1}s^{-1}$ Specific Ka values for certain peptides of the invention are described herein (Ka of $2.26 \times 10^5$ $M^{-1}s^{-1}$). The peptide clearing agents of the invention may display off rates (disassociation rate constants, Kd) of anywhere between around $1 \times 10^{-5}$ $s^{-1}$ and $1 \times 10^{-1}$ $s^{-1}$ in certain embodiments, or between around $1 \times 10^{-4}$ $s^{-1}$ and $1 \times 10^{-2}$ $s^{-1}$, or between around $1 \times 10^{-3}$ $s^{-1}$ and $5 \times 10^{-3}$ $s^{-1}$. Specific Kd values for certain peptides of the invention are described herein (Kd of $1.14 \times 10^{-3}$ $s^{-1}$).

Thus, the peptide clearing agents of the invention may display derived equilibrium association constants (KA) according to the 1:1 Langmuir model of anywhere between around $1 \times 10^6$ $M^{-1}$ and $1 \times 10^{10}$ $M^{-1}$ in certain embodiments, or between around $1 \times 10^7$ $M^{-1}$ and $1 \times 10^9$ $M^{-1}$, or between around $1 \times 10^6$ $M^{-1}$ and $5 \times 10^8$ $M^{-1}$. Specific KA values for certain peptides of the invention are described herein (around $1.98 \times 10^8$ $M^{-1}$). This may result in a dissociation constant for the peptide clearing agents of the invention in the region of anywhere between around $1 \times 10^{-7}$ M and $1 \times 10^{-11}$ M in certain embodiments, or between around $1 \times 10^{-8}$ M and $1 \times 10^{-10}$ M, or between around $4 \times 10^{-9}$ M and $6 \times 10^{-9}$ M. A specific KD value for certain peptides of the invention is described herein (around $5.04 \times 10^{-9}$ M).

Alternatively, in specific embodiments, the data may be obtained using commercially available Biaevaluation software using a two state binding model. The peptide clearing agents of the invention may thus display first order on rates (association rate constants, Ka1) of anywhere between around $1 \times 10^3$ $M^{-1}s^{-1}$ and $1 \times 10^7$ $M^{-1}s^{-1}$ in certain embodiments, or between around $1 \times 10^4$ $M^{-1}s^{-1}$ and $1 \times 10^6$ $M^{-1}s^{-1}$ or between $1 \times 10^5$ $M^{-1}s^{-1}$ and $5 \times 10^5$ $M^{-1}S^{-1}$. Specific Ka1 values for certain peptides of the invention are described herein (Ka1 of $2.84 \times 10^5$ $M^{-1}s^{-1}$). The peptide clearing agents of the invention may thus display second order on rates (association rate constants, Ka2) of anywhere between around $0.001$ $s^{-1}$ and $1$ $s^{-1}$ in certain embodiments, or between around $0.01$ $s^{-1}$ and $0.1$ $s^{-1}$ or between around $0.01$ $s^{-1}$ and $0.05$ $s^{-1}$ or $0.02$ $s^{-1}$. Specific Ka2 values for certain peptides of the invention are described herein (Ka2 of $0.014$ $s^{-1}$).

The peptide clearing agents of the invention may display first order off rates (disassociation rate constants, Kd1) of anywhere between around $0.001$ $s^{-1}$ and $1$ $s^{-1}$ in certain embodiments, or between around $0.01$ $s^{-1}$ and $0.1$ $s^{-1}$ or between around $0.01$ $s^{-1}$ and $0.05$ $s^{-1}$ or $0.03$ $s^{-1}$. Specific Kd1 values for certain peptides of the invention are described herein (Kd1 of $0.0258$ $s^{-1}$). The peptide clearing agents of the invention may display second order off rates (disassociation rate constants, Kd2) of anywhere between around $1 \times 10^{-5}$ $s^{-1}$ and $1 \times 10^{-1}$ $s^{-1}$ in certain embodiments, or between around $1 \times 10^{-4}$ $s^{-1}$ and $1 \times 10^{-2}$ $s^{-1}$ or between around $1 \times 10^{-3}$ $s^{-1}$ and $5 \times 10^{-3}$ $s^{-1}$. Specific Kd2 values for certain peptides of the invention are described herein (Kd2 of $1.58 \times 10^{-3}$ $s^{-1}$).

The peptide clearing agents of the invention may display derived equilibrium association constants (K), based upon the two state binding model fit, of anywhere between around $1 \times 10^5$ $M^{-1}$ and $1 \times 10^{10}$ $M^{-1}$ in certain embodiments, or between around $1 \times 10^7$ $M^{-1}$ and $1 \times 10^9$ $M^{-1}$, or between around $1 \times 10^8$ $M^{-1}$ and $2 \times 10^8$ $M^{-1}$. Specific K values for certain peptides of the invention are described herein (around $1.09 \times 10^8$ $M^{-1}$). This may result in a dissociation constant for the peptide clearing agents of the invention in the region of anywhere between around $1 \times 10^{-5}$ M and $1 \times 10^{-10}$ M in certain embodiments, or between around $1 \times 10^{-7}$ M and $1 \times 10^{-9}$ M. An averaged specific KD value for certain peptides of the invention is described herein (around 9 nM) based upon the two state reaction fit.

Peptide clearing agents of the invention have also been found to have suitable abilities to inhibit enzyme activity. Thus, the peptide clearing agents of the invention may display a half maximal inhibitory concentration ($IC_{50}$) on the micromolar scale. Suitable peptides may display an $IC_{50}$ of around 10 to around 1000 µM, more specifically between around 20 and 200 µM, such as between around 50 and 150 µM.

As discussed above, the peptide binds to the conjugate of binding molecule and enzyme, and in specific embodiments the enzyme, especially the active site of the enzyme. Thus, in certain embodiments, the peptide binds the active site of the enzyme with sufficiently high affinity to act as a means of inactivating or blocking the enzyme activity, as well as directing it to the liver. In preferred embodiments, the peptide is resistant to enzyme activity, even though it fits into the active site. Suitable peptides which bind to the enzyme, but which do not act as substrates for enzyme activity are described in detail herein. Thus, the sequence and structure of the peptide clearing agent of the invention is typically determined by the active site of the enzyme of interest. In certain embodiments, the peptide is a substrate analogue which binds the active site but is not converted by the enzyme. Thus, the starting point for the peptide may be the sequence of the substrate molecule, which may then be modified accordingly to produce a peptide clearing agent.

For example, the natural substrate of CPG2 is folic acid. Folic acid is a molecule consisting of pteroic acid linked via an amide bond to glutamic acid. CPG2 hydrolyses the glutamate-pteroic acid amide bond. Thus, the peptide of the invention may be based upon this structure. In specific embodiments, the peptide comprises the glutamate residue, but in the D-form (as opposed to the naturally occurring L-form). The peptide of the invention may comprise the sequence—Tryptophan-phenylalanine-glutamate (WFE), optionally incorporating glutamate as a D-amino acid rather than an L-amino acid. Inclusion of the D-form amino acid is with a view to preventing lysis of the glutamate-phenylalanine peptide bond by CPG2. This sequence has the closest structural resemblance to folic acid possible with a tripeptide, having a bicyclic nitrogen substituted ring structure at the amino end, a six-membered aromatic ring in the middle and glutamate at the carboxy end. The peptides of the invention may represent variations on this basic amino acid sequence. Conservative substitutions may be made such as replacing amino acids with other amino acids of the same or similar charge or hydrophobicity or size for example, as would be apparent to one skilled in the art. Thus, for example, amino acids such as glycine, alanine, valine, leucine and isoleucine which each have aliphatic side chains may be substituted for one another in certain embodiments. Phenylalanine, tyrosine and tryptophan each have aromatic side chains and may thus be substituted for one another in certain embodiments. Cysteine and methionine both have sulphur-containing side chains and may thus be substituted for one another in certain embodiments. Serine and threonine have aliphatic hydroxyl side chains and thus may be substituted for one another in certain embodiments. Lysine, arginine and histidine have basic side chains and thus may be substituted for one another in certain embodiments. Aspartate and glutamate are both acidic and may be substituted for one another in certain embodiments. Similarly, their amide derivatives, asparagine and glutamine may be substituted for one another in certain embodiments. Non-natural amino acids may be introduced with a view to improving binding to the (active site of the) enzyme. Many non-natural amino acids are known in the art, having well characterised molecular structures, which can be readily incorporated into a synthesised peptide with a view to improving binding characteristics. Examples include 2-Aminoadipic acid (Aad), 2-Aminoadipic acid (bAad), beta-Alanine, beta-Aminopropionic acid (bAla), 2-Aminobutyric acid (Abu), 4-Aminobutyric acid, piperidinic acid (4Abu), 6-Aminocaproic acid (Acp), 2-Aminoheptanoic acid (Ahe), 2-Aminoisobutyric acid (Aib), 3-Aminoisobutyric acid (bAib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylsine (aHyl), 3-Hydroxyproline (3Hyp), 4-Hydroxyproline (4Hyp), Isodesmosine (Ide), allo-Isoleucine (aIle), N-Methylglycine, sarcosine (MeGly), N-Methylisoleucine (Meile), 6-N-Methyllysine (MeLys), N-Methylvaline (MeVal), Norvaline (Nva), Norleucine (Nle) and Ornithine (Orn).

Specific peptide clearing agents of the invention which bind to CPG2 and effectively inhibit enzyme activity are described herein. Such peptides may comprise, consist essentially of or consist of the following amino acid sequence:
Amino-Naphthoic Acid (ANA)-Glutamate (Glu)

The peptides of the invention may comprise, consist essentially of or consist of a dipeptide of formula I:

(I)

Such a dipeptide is shown herein to display the desired properties associated with a clearing agent of the invention. The peptide has nanomolar affinity for the active site of CPG2 and is not acted upon as a substrate. The $IC_{50}$ is on the micromolar scale, between 50 and 150 μM, more specifically around 88.5 μM. As described herein, the peptide, in addition to binding the active site of the enzyme, must also bind to the asialoglycoprotein receptor expressed by hepatic cells to facilitate clearance through the liver. Thus, this basic dipeptide may be extended to permit clearance, as discussed herein. Such peptides may be 3, 4, 5, 6, 7, 8, 9 or 10 or more amino acids in length and may be glycosylated.

In specific embodiments of the invention, the peptide comprises, consists essentially of or consists of the amino acid sequence:
Serine (Ser)-Alanine (Ala)-Amino-Naphthoic Acid (ANA)-Glutamate (Glu) (SEQ ID NO: 1).

The peptide may be modified to facilitate clearance. The peptide may be glycosylated at a suitable residue to permit binding to hepatic cells expressing the asialoglycoprotein receptor. In specific embodiments the serine residue is glycosylated. The peptide may comprise additional amino acid residues, as discussed herein, up to a maximum of 10, 20 or 30 amino acids as appropriate, such as a total length of 4, 5, 6, 7, 8, 9 or 10 amino acids. The peptides of the invention may comprise, consist essentially of or consist of a peptide of formula II:

(II)

Such a peptide is shown herein to display the desired properties associated with a clearing agent of the invention. The peptide has nanomolar affinity for the active site of CPG2 and is not acted upon as a substrate. The $IC_{50}$ is on the micromolar scale, between 50 and 150 μM, more specifically around 110 μM. As discussed above, the peptides of the invention may contain D-form amino acids as opposed to the naturally occurring L-form (different optical isomers). In particular, the glutamate residue may be provided in the D-form. Also as discussed herein, substitutions and in particular conservative substitutions may be made to any of the amino acids in the peptide, provided functionality as a peptide clearing agent of the invention is retained.

The peptides of the invention offer advantages over antibody based clearing agents as they are minimally immunogenic. This is due to their relatively short length. Each peptide clearing agent of the invention comprises of two distinct domains, despite their typically small size. The first domain comprises the short sequence of amino acids which bind into the active site of the target enzyme, but without being covalently altered by the action of the enzyme (as discussed above). This domain may include non-natural amino acids, such as D-form amino acids, which prevent the enzyme acting on the peptide once bound into the active site. Thus, in certain embodiments, the first domain of the peptide of the invention is no more than 10, 15 or 20 amino acids in length. In more specific embodiments, the first domain of the peptide is between 3 and 10 amino acids in length, such as 3, 4, 5, 6, 7, 8, 9 or 10 amino acids in length. In a specific embodiment, the peptides, or first domain thereof, are heptapeptides.

The second domain binds to the asialoglycoprotein receptor expressed by hepatic cells. This leads to internalisation of the conjugate found at a non-target location. Thus, binding of the peptide to the asialoglycoprotein receptor expressed by hepatic cells facilitates clearance of the peptide. In specific embodiments, the peptide comprises either a continuation of the amino acid sequence or an alternative chemical structure attachment. Each carries one or more pendant sugar, preferably galactose, groups capable of binding and uptake by hepatic cells bearing the asialoglycoprotein receptor. Thus, in specific embodiments, glycosylation of the peptide clearing agent of the invention involves coupling of one or more galactose groups. In specific embodiments, the second domain comprises one or more galactosyl serine amino acids (i.e. galactose covalently linked to the O residue of the serine hydroxyl group) to generate O-linked glycosyl peptides. This substance is commercially available from a number of suppliers. Any number of these extra galactosyl serine groups can be added by known peptide chemistry techniques, to strengthen the binding of the glycosyl peptide to the asialoglycoprotein receptor of liver cells (hepatocytes) as needed. The galactosyl serine can be added directly to the (first domain of the) peptide or via a linker amino acid or stretch of amino acids. The linker may thus comprise one or more amino acids, in particular glycine residues. Multiple galactose moieties may be added, each separated by one or more spacer amino acids. Thus, the spaces between further galactosyl serine residues can be constructed with one or more further amino acids so as to optimize the orientation and disposition of the galactosyl groups. Of course, alternative galactosyl amino acids can be used in place of galactosyl serine as appropriate.

It is also important that the amino acid sequence of the peptide does not mimic any active peptides of the (human) subject; otherwise it may have undesired biological activity. Moreover, the peptide should not bind to (the active sites of) any endogenous (human) proteins which may result in undesired activity, in particular enzymes or receptors. Candidates may be identified using amino acid sequence database searches and then tested using appropriate in vitro testing for example.

Typically, the peptides of the invention are chemically synthesized. However, recombinantly produced peptides may be employed, as desired. Recombinantly produced peptides may be subsequently glycosylated following expression, or may be glyscoylated in the cell if an appropriate cell type is selected to direct expression. Suitable reaction schemes for producing the peptide clearing agents of the invention are described in greater detail herein, with reference to the experimental examples.

The peptides of the invention may be produced by any suitable technique. They may be produced by means of random peptide libraries arrayed on the surface of genetically engineered viruses or cells (phage display, two-hybrid systems etc.), or synthesized and arrayed on structured surfaces (e.g. PEPSCAN libraries). The target enzyme will be exposed in aqueous solution to such surfaces upon which the peptide is arrayed, according to PEPSCAN protocols, which will then be processed to detect binding of the enzyme to the surface via the displayed peptide. The first rounds of this procedure may result in only weak binding, but positive binding sequences may then be used as starting points for further modifications including extension to produce longer peptides. These longer peptides can then be screened and improved binders further modified through systematic changes in amino acids in each position of the sequence to produce optimized peptides. Certain changes result in slightly higher binding efficiency, and then these slightly improved sequences are used as further starting points for yet more cycles of systematic substitution, until binding sequences with the desired affinity and specificity emerge. Subsequently, the sugar-bearing domains can be added in order to complete the construction. Manufacture of these substances can be accomplished by known, standard methods of peptide synthesis and glycosylation.

Thus, the invention also provides a method of producing a(n optimized) peptide clearing agent of the invention comprising:
  a. preparing an array of peptides, optionally based upon a starting peptide which is a structural analogue of the enzyme substrate
  b. screening the array of peptides for binding affinity for the conjugate of an enzyme and a binding molecule which binds specifically at a target location and selecting those with binding affinity
  c. optionally modifying the amino acid sequence of the peptides with binding affinity in step b and repeating step b using the modified peptides to test for an improvement in binding affinity
  d. optionally performing a substitution at each residue of the modified peptides found in step c to have improved binding affinity and repeating step b to determine if any of the substituted peptides have further improved binding affinity
  e. optionally determining whether the peptides resulting from step c or d (with improved binding affinity) have the ability to prevent or inhibit enzyme activity
  f. optionally confirming binding specificity for the enzyme by testing with a range of control proteins from the subject
  g. testing the peptides for the ability to bind to the asialoglycoprotein receptor expressed by hepatic cells to facilitate clearance through the liver
  wherein steps e and f, if performed, can be carried out in either order and step g can be carried out at any point in the method, including providing an array of peptides in step a capable of binding to the asialoglycoprotein receptor expressed by hepatic cells to facilitate clearance through the liver.

The peptides in step g may be modified to ensure that they can bind to the asialoglycoprotein receptor expressed by hepatic cells to facilitate clearance through the liver. Thus, in specific embodiments of the method step g comprises glycosylating the peptide or peptides. Step a may therefore comprise providing an array of glycosylated peptides.

The array of peptides is thus typically immobilized on a solid surface, such as in the well of a multi-well plate, in PEPSCAN type embodiments. Any suitable solid surface may be employed. Synthesis of the peptide may occur on the solid surface or the peptides may be synthesised and subsequently immobilised. Alternatively, in phage display type embodiments or related technologies, the enzyme (or conjugate of binding molecule and enzyme) is the entity that is immobilized and the phage display library is screened against the immobilized enzyme.

The array of peptides may comprise a peptide library. Phage display or related technologies may rely on essentially random peptide libraries which are displayed and screened against the enzyme in several rounds to identify the strongest binders. In certain embodiments, the starting peptide is a short peptide designed to bind to the conjugate of binding molecule and enzyme, and in specific embodiments the enzyme, especially the active site of the enzyme. The starting sequence and structure of the peptides may be determined by the shape of the active site of the enzyme of interest. In certain embodiments, the starting peptides are predicted substrate analogues which may bind the active site but are not converted by the enzyme. Thus, the starting point for the peptide may be the sequence or structure of the substrate molecule, which may then be modified according to the methods of the invention to produce a peptide clearing agent. In specific embodiments, it may be a tripeptide. For example, as discussed above the natural substrate of CPG2 is folic acid. Thus, the starting point for the methods may be based upon this structure. In specific embodiments, the peptide starting point comprises the glutamate residue found in folic acid, but in the D-form (as opposed to the usual L-form). The starting point peptide may comprise the sequence—Tryptophan-phenylalanine-glutamate (WFE), optionally incorporating glutamate as a D-amino acid rather than an L-amino acid. Alternatively, the starting point could be the dipeptide ANA-Glu or the peptide of SEQ ID NO:1 (Ser-Ala-ANA-Glu). The methods of the invention may then systematically modify this starting sequence to produce peptide clearing agents with the desired properties. Thus, the peptide array or library may include the tripeptide WFE together with a range of tripeptide derivatives. The derivatives may comprise peptides with systematic substitution of all amino acids or may include only conservatively substituted amino acids for example (as defined herein).

Step b involves screening the array of peptides for binding affinity for the conjugate of an enzyme and a binding molecule which binds specifically at a target location and selecting those with binding affinity. As indicated, screening for binding is typically screening for binding to the enzyme active site. Any suitable screen may be employed. In phage display type embodiments, the screen is based upon binding. Any unbound phage is washed away in a washing step. Step b can be repeated a number of times, following phage elution and further infection to produce more phage, to permit enrichment of phage expressing a binding peptide. The sequence of the peptide that is capable of binding the enzyme can then be readily determined based upon the sequence expressed by the phage. The peptide recovered can then be modified if desired, according to the further steps of the method.

In PEPSCAN type embodiments, the enzyme (or enzyme-binding molecule conjugate) may be labelled with a label. If the peptide binds the enzyme it will become immobilized. Following a wash step, a reporter is added, that binds either to the enzyme directly or to the label if the enzyme is labelled. The reporter may itself be an enzyme, such as alkaline phosphatase for example. The reporter does not necessarily bind the enzyme or label itself, it may similarly be attached to a binding molecule which binds the label or enzyme. Thus, in specific embodiments, the enzyme is labelled with biotin. The reporter is attached to an avidin molecule, such as streptavidin. Interaction between biotin and streptavidin effectively localises reporter activity to the site of the enzyme, thus revealing the location of a peptide that successfully bound the enzyme (following the appropriate wash steps). A specific example of the method is set forth in example 1.

Optional step c typically involves extension of the peptide amino acid sequence in an attempt to improve binding affinity. Other modifications may, however, be made such as substitutions with non-natural amino acids to replace the existing amino acids. The extension may be by 1, 2, 3, 4 or 5 amino acids at a time in certain embodiments. The thus extended peptides are then re-tested according to step b to determine which modifications lead to an improvement in binding affinity.

Step d is then a full positional scan of the peptide or peptides resulting from step c which display improved binding properties. By "full positional scan" is meant that each individual amino acid is substituted to produce a range of peptides to determine whether binding may be further improved. This produces a peptide or peptides with optimal binding affinity for the target enzyme.

Further testing may then be carried out. Thus, the peptide or peptides may be tested to determine whether the peptides with improved binding affinity for the conjugate also have the ability to prevent or inhibit enzyme activity. Where the peptides have been designed to bind the active site, as discussed herein, this step may not be necessary as the screen (which tests for binding affinity) may prevent those peptides which are acted upon by the enzyme from producing a positive result.

As discussed above, it is also important that the amino acid sequence of the peptide does not mimic any active peptides of the (human) subject; otherwise it may have undesired biological activity. Moreover, the peptide should not bind the active sites of any endogenous (human) enzymes. Thus, the methods of the invention may comprise optionally confirming binding specificity for the enzyme by testing with a range of control proteins from the subject. Suitable controls may be determined based upon the enzyme of interest. Proteins having similar active sites and/or primary amino acid sequences may be identified for example using amino acid sequence or structural database searches and tested accordingly for binding. Additionally or alternatively, the peptide may be tested in a suitable animal model to determine whether there are any adverse effects. In specific embodiments, the method further comprises comparing the amino acid sequence of the peptide produced by the method with a human amino acid sequence database to confirm the peptide is unlikely to have an undesired biological activity.

The peptide (or peptides) binds (or bind) to the asialoglycoprotein receptor expressed by hepatic cells. This leads to internalisation of the conjugate found at a non-target location. Thus, binding of the peptide to the asialoglycoprotein receptor expressed by hepatic cells facilitates clearance of the peptide. In specific embodiments, the peptide or peptides are glycosylated in order to be useful as clearing agents in the invention. This may occur at any point in the methods. Typically this occurs once one or more suitable candidates have been produced according to the methods of the invention. It may occur prior to further testing of the peptide or peptides. Particularly in phage display type embodiments, glycosylation occurs following isolation of candidate binding peptides—the peptides expressed by the phage will not be glycosylated. In alternative embodiments, the starting peptides may be glycosylated or the peptides may be glycosylated prior to steps b or d. Glycosylation may be achieved through any suitable means, examples of which are discussed herein (which discussion applies mutatis mutandis).

The peptide clearing agents of the invention are particularly applicable to treatment methods, such as ADEPT, in which an enzyme is used to convert a prodrug to an active drug through localisation of the enzyme via a conjugate of a binding molecule and the enzyme. Thus the invention also provides for a treatment method, such as ADEPT, in which an enzyme is used to convert a prodrug to an active drug through localisation of the enzyme via a conjugate of a binding molecule and the enzyme in which a peptide clearing agent of the invention is employed. Similarly, the invention provides for use of a peptide of the invention as a clearing agent in a treatment method in which an enzyme is used to convert a prodrug to an active drug through localisation of the enzyme via a conjugate of a binding molecule and the enzyme, in particular in antibody directed enzyme pro-drug therapy (ADEPT). These aspects may also be coined in terms of medical use. Thus, the invention provides a peptide of the invention for use as a clearing agent in a treatment method in which an enzyme is used to convert a prodrug to an active drug through localisation of the enzyme via a conjugate of a binding molecule and the enzyme, in particular in antibody directed enzyme pro-drug therapy (ADEPT). Similarly, the invention provides for use of a peptide of the invention in the manufacture of a clearing agent for use in a treatment method in which an enzyme is used to convert a prodrug to an active drug through localisation of the enzyme via a conjugate of a binding molecule and the enzyme, in particular for use in antibody directed enzyme pro-drug therapy (ADEPT).

BRIEF DESCRIPTION OF THE DRAWINGS

FIG. 11a/b shows flow cytometry results of a control against auto-fluorescence with a control (CEA surface antigen negative) cell line (CRL 1573).

FIG. 11c/d shows flow cytometry results for a control against CPG2-PE binding with a control (CEA surface antigen negative) cell line (CRL 1573).

FIG. 11g/h shows flow cytometry results for a control against sheep anti-CEA-PE binding with a control (CEA surface antigen negative) cell line (CRL 1573).

FIG. 11i/j shows flow cytometry results for a control against A5B5 anti-CEA+goat anti-mouse-PE binding with a control (CEA surface antigen negative) cell line (CRL 1573)

Figure 1:
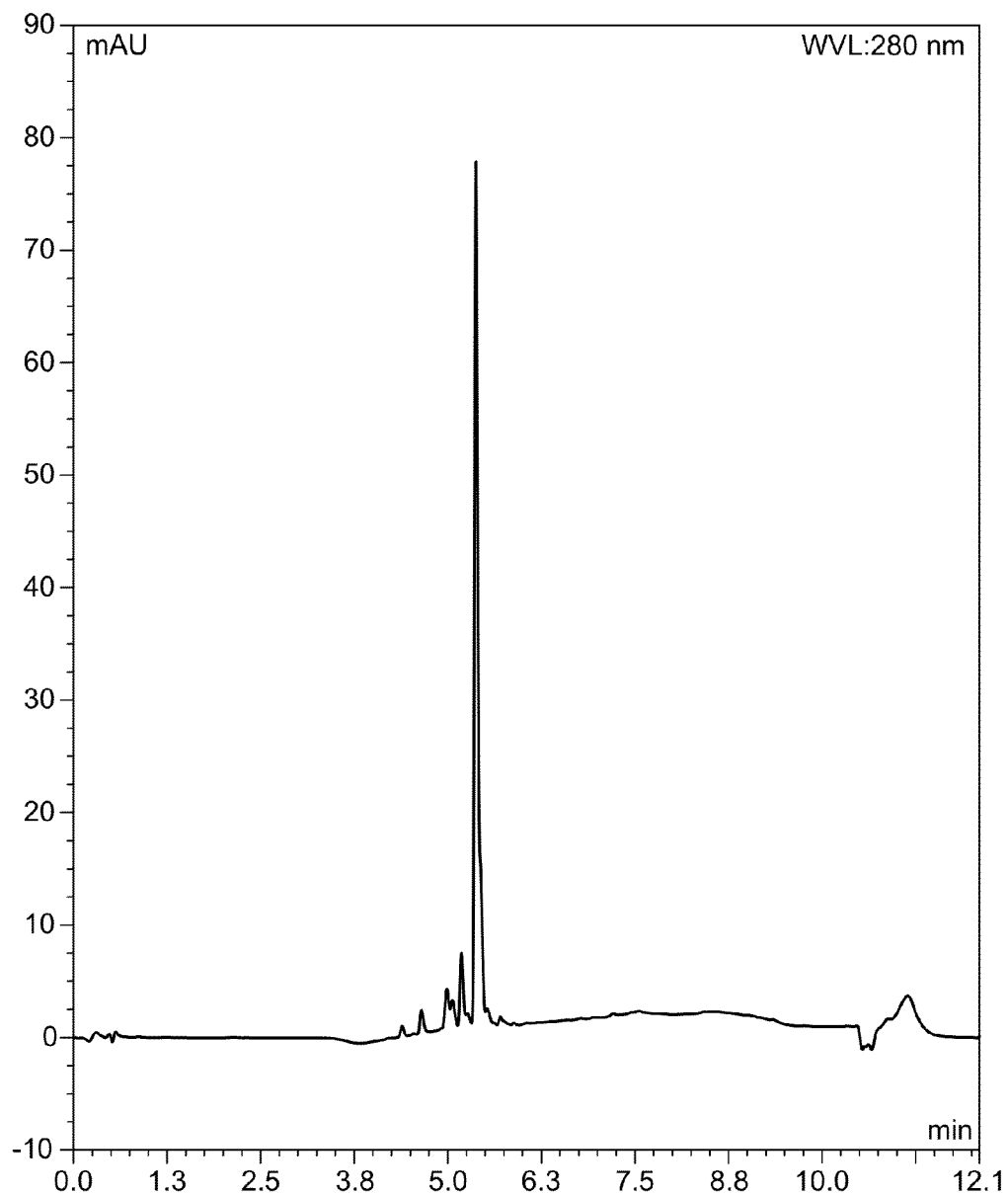
FIG. 1: HPLC spectrum of the CP014 galactose moiety acetylated product

The invention will be described with reference to the following non-limiting examples:

Example 1

Generation of a Clearing Agent Comprising a Glycosylated Binder Peptide for the Enzyme CPG2

A library of tripeptides is synthesised in the form of the PEPSCAN technology (2 & 3). The peptides are synthesized by robotic means attached to the inside surfaces of plastic wells. The first peptide in the series is based on the structure folic acid, which is the natural substrate for CPG2. Folic acid is a molecule consisting of pteroic acid linked via an amide bond to glutamic acid. CPG2 hydrolyses the glutamate-pteroic acid amide bond. This first tripeptide has the following sequence—Tryptophan-phenylalanine-glutamate (WFE), but the glutamate is a D-amino acid rather than an L-amino acid because it is intended that the glutamate-phenyalanine peptide bond should not be subject to lysis by CPG2. This sequence is chosen as it has the closest resemblance to folic acid possible with a tripeptide, having a bicyclic nitrogen substituted ring structure at the amino end, a six-membered aromatic ring in the middle and glutamate at the carboxy end. The rest of the tripeptide library consists of peptides that are systematically varied from this starting structure by the substitution of all possible amino acids in each of the three positions.

An aqueous solution of a CPG2-biotin conjugate (0.1 ug/ml) in phosphate buffered saline containing Tween 20 (0.05% v/v) and bovine serum albumin (0.1% w/v) (PBSTA) is dispensed into each of the wells and allowed to incubate for 60 minutes, after which the wells are emptied and rinsed. All of the wells are then dosed with a solution of a streptavidin-alkaline phosphatase conjugate (1 ug/ml) in PBSTA plus 0.5 mM magnesium chloride and incubated for another 60 minutes, after which the wells are again emptied and washed. In the next assay step, a solution of substrate for the alkaline phosphatase (para-nitrophenol phosphate) in diethanolamine (105 ml in 600 ml purified water) at 1 mg/ml is dosed into the wells, and these are incubated for a further 60 minutes, or until some colour has developed, for up to 48 hours. Finally, the wells are assessed for colour generation in a special reader, in terms of optical density readings at a wavelength 405 nm.

The presence of colour in a well indicates that the peptide attached to the well surface has bound the biotinylated CPG2 enzyme without itself being hydrolysed, and the strength of the colour is directly proportional to the amount of CPG2 that has bound, indicating the strength of binding (affinity).

The sequences that have bound CPG2 are noted and ranked. The highest binding sequence is then used as a starting point for making an array of extended peptides in which all possible variations of dipeptides are attached to the binding tripeptide, in the same manner as the first array of peptides was created. The same assay procedure for the detection of CPG2 binding is applied again to these wells, and the strongest binders again identified and ranked.

The entire procedure is repeated again to add a further two amino acid extensions to identify the strongest binding heptapeptides. The strongest binder is then subjected to a full positional scan to determine whether any variations of the best binding sequence can give still stronger binding.

At any step in this sequence of assay steps, it is possible to go to the next strongest binder and create peptide variations of that sequence, which is a procedure that can be followed if a stronger binder is not detected in the library derived from the strongest candidate.

It will be appreciated that the basic peptide selection technique (PEPSCAN) described here can be varied in many different ways, in order to discover binding peptides. The example method described here is just one of the possible ways in which the methods can be used.

Once a satisfactory binding sequence has been found, samples of the free peptide can be synthesized in sufficient quantity to undertake further experimentation and development. In particular, variants can be made with extensions at either end, consisting of one or more galactosyl serine amino acids (i.e. galactose covalently linked to the O residue of the serine hydroxyl group, which is commercially available from a number of suppliers) to generate O-linked glycosyl peptides. Any number of these extra galactosyl serine groups can be added by known peptide chemistry techniques, to strengthen the binding of the glycosyl peptide to the asialoglycoprotein receptor of liver cells (hepatocytes) as needed. This binding can be modeled in-vitro by the use of isolated C-type lectin or by isolated rat hepatocytes.

The galactosyl serine can be added directly to the heptapeptide or via a linker amino acid or stretch of amino acids, preferably (but not necessarily) composed of one or more glycine residues. The spaces between further galactosyl serine residues can be constructed with one or more further amino acids so as to optimize the orientation and disposition of the galactosyl groups.

Other galactosyl amino acids can be used in place of galactosyl serine, if they are readily available and are amenable to the peptide synthesis chemistry.

A number of CPG2-binding peptides can be developed in this way to create a range of candidate molecules. Each candidate molecule can then be subjected to further rounds of characterization and selection in terms of binding to hepatic cells, binding to CPG2, stability to proteases, stability in storage, lack of toxicity etc. A range of these peptides will be generated, in order to select peptides with affinity for CPG2 that is matched with the affinity of the targeting molecule that binds to the cancer antigen (i.e. an affinity that is approximately 10 fold lower than the affinity of the targeting antibody for the cancer antigen).

Example 2

Clearing Agent Enzyme Binder CP014

Chemical Description and Graphical Representation of the Compound Designated CP014

Compound of formula II: CP014 H-Ser(Gal)-Ala-ANA-Glu-OH

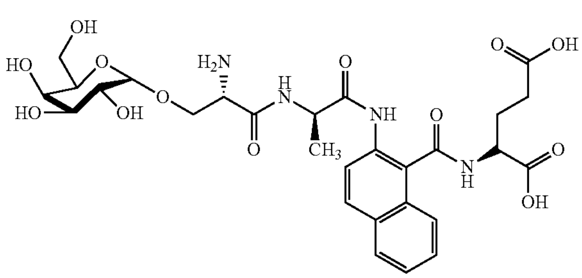

Method of Synthesis and Purification

Peptide CP014 was synthesised by solid phase peptide synthesis (SPPS) using a CEM Liberty Microwave Synthesiser and by application of Fmoc chemistry (Scheme 1 where R=resin). The resin Fmoc-Glu(OtBu)-NovaSynTGA (MerckBioscience) was employed on a scale of 0.1 mmol. All subsequent Fmoc-building blocks were purchased from NeoMPS, Bachem and MerckBioscience. The FMoc-serine galactose (acetyl protected) was obtained from Dextra Labs.

SPPS Step 1

Scheme 1: (i) Coupling conditions: HBTU, DMF, DIEA, NMP, 90 mins.

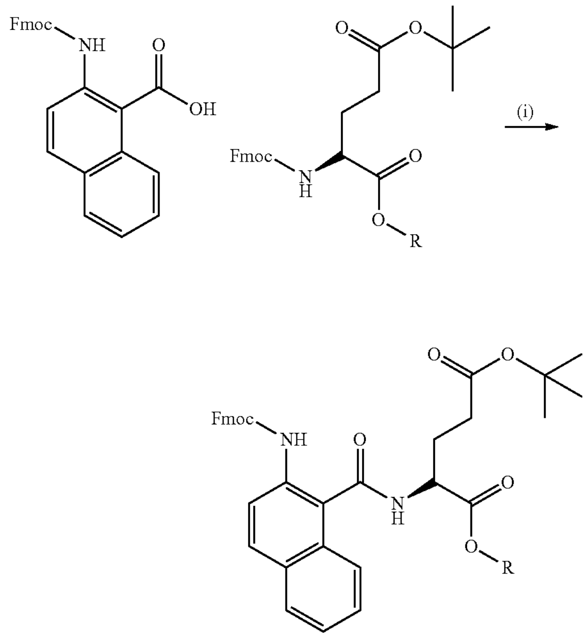

SPPS Step 2

Scheme 2: (i) Coupling conditions: BTC, collidine, THF, MW, 50° C.

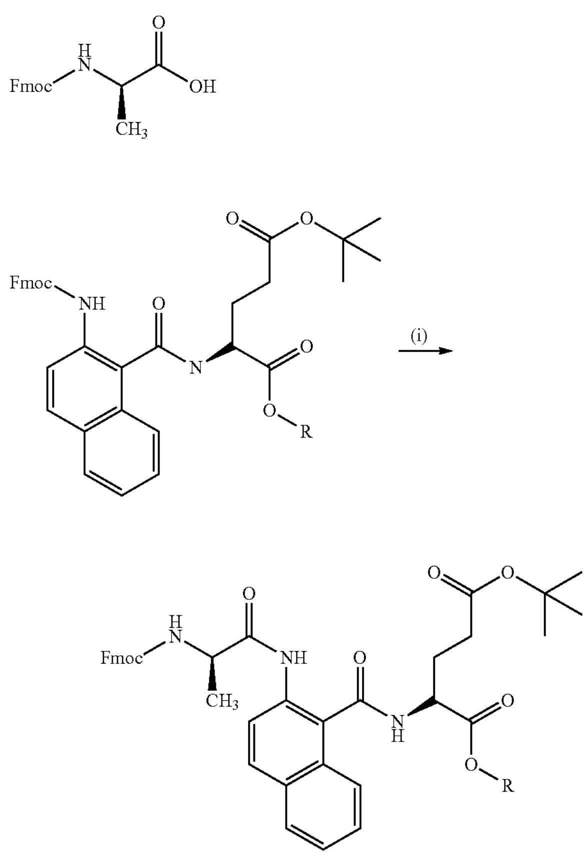

SPPS Step 3

Scheme 3: Coupling conditions: PyBoP, HOBt, DIPEA, DMF, MW.

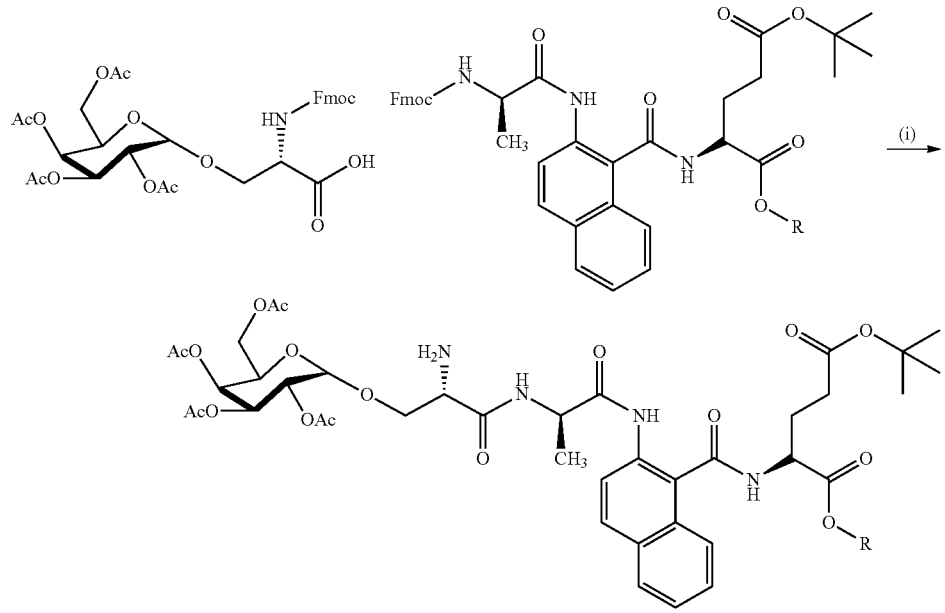

Cleavage of Peptide from Resin and Purification

Figure 2:
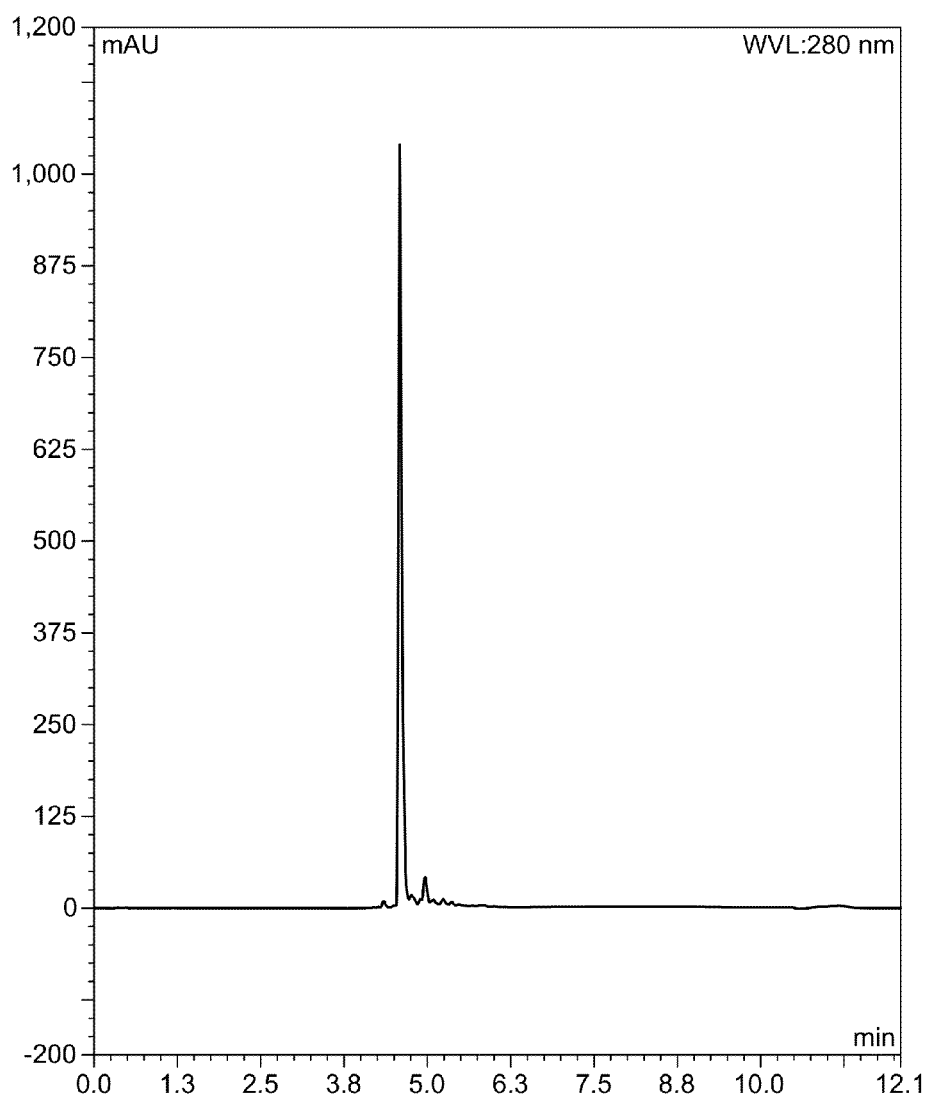
FIG. 2: HPLC spectrum of the CP014 galactose moiety deacetylated product

On completion of the synthesis the resin was washed with DCM (10 mL) and EtOH (10 mL) and dried in a desiccator for 24 h. After 24 h the completed peptide was removed from the desiccator and subjected to a 10 mL solution of 95% TFA, 2.5% d.H$_2$O, and 2.5% TIPS for 3 h. After this time, the reaction was evaporated under reduced pressure to afford a colourless oil. The oil was precipitated in cold TBME to yield a crude brown solid (Scheme 4). The crude product was dissolved in 500 µL of 50% MeCN in d.H$_2$O and then further diluted with 600 µL of 5% MeCN (0.1% TFA), then filtered and purified employing a reverse phase program on an Onyx C18 column and applying a gradient elution of 5 to 100% MeCN (0.1% TFA) over 12 minutes. The retention time for the product collection was 5.6 minutes at 280 nm (FIG. 2). The collected fractions were combined and reduced under pressure to afford a brown oil which was dissolved in d.H$_2$O (4 mL) and subjected to freeze drying at 0.2 mBar for 18 h to afford a brown solid.

Scheme 4: (i) Cleavage conditions: TFA, TIPS, d.H$_2$O, rt. 3 h.

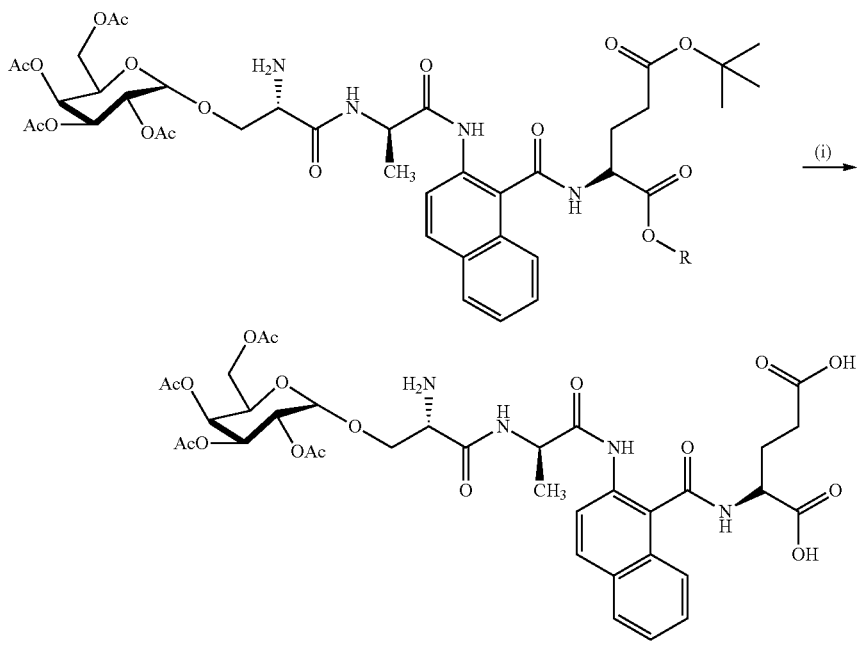

Removal of Acetyl Protection from Galactose Moiety and Purification

Figure 3:
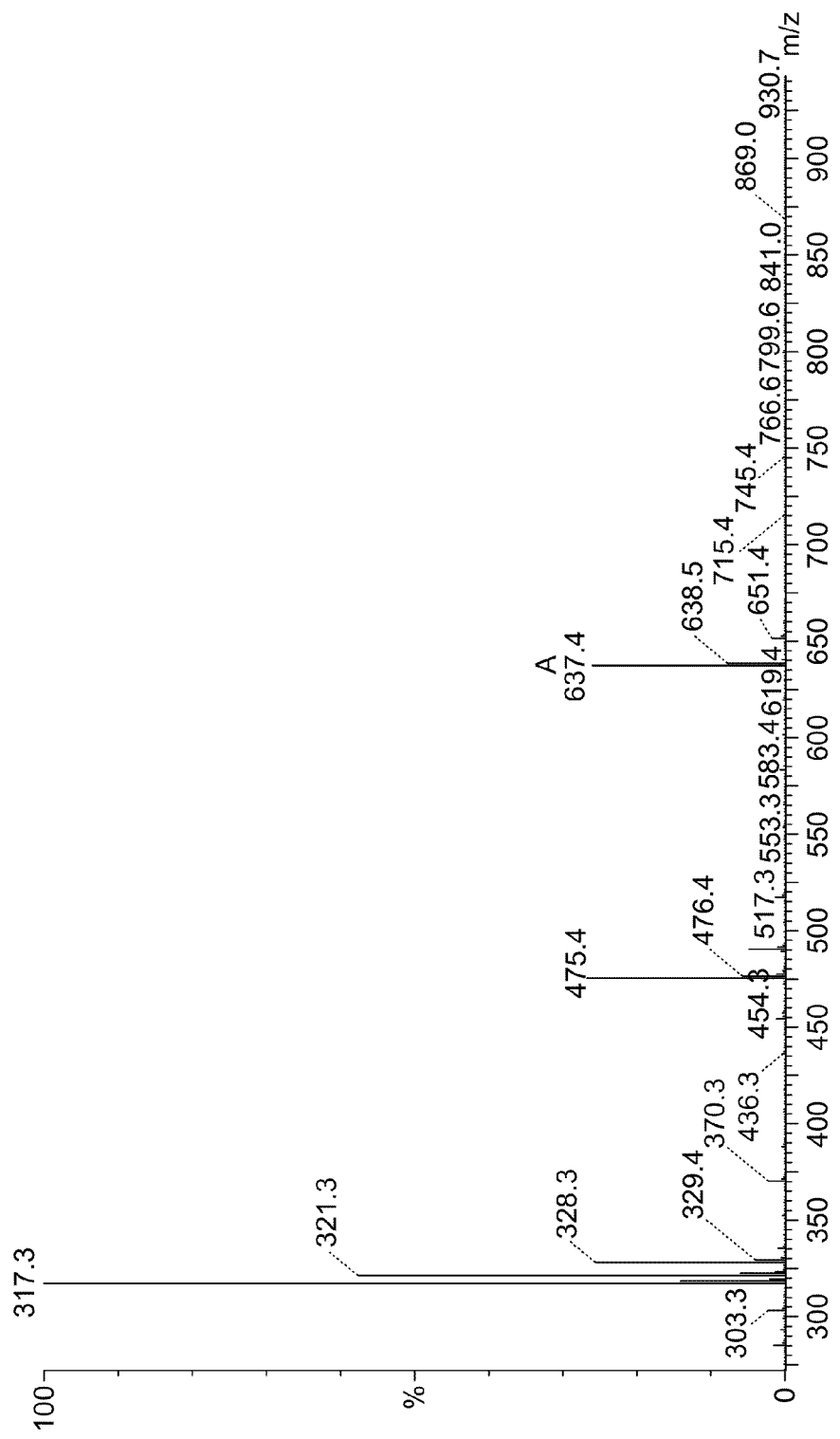
FIG. 3: ESI Data (electrospray mass spectrometry) confirming the structure of CP014

Removal of the acetyl protection from the galactose moiety was achieved by dissolving the product in a minimum amount of anhydrous MeOH and then by addition of a 1 M solution of NaOMe in anhydrous MeOH drop-wise to pH 9-10. The reaction was then allowed to stir for 1 h. After this time, acetic acid was added drop-wise to pH 7 and the volatiles removed under reduced pressure to afford a brown solid (Scheme 5). The product was dissolved in 500 μL of 50% MeCN in d.H$_2$O and then further diluted with 600 μL of 5% MeCN (0.1% TFA), filtered and purified using a standard reverse phase program on an Onyx C18 column and applying a gradient elution of 5 to 100% MeCN (0.1% TFA) over 12 minutes. The retention time for the product collection was 4.7 minutes at 280 nm (FIG. 3). The collected fractions were combined and reduced under pressure to afford a brown solid which was dissolved in d.H$_2$O (4 mL) and subjected to freeze drying conditions at 0.2 mBar for 18 h to afford a brown solid.

aliquots of this solution were added to cuvettes and assay buffer was added to adjust the volume of solution in each cuvette to 900 μL. 100 μL aliquots of 0.6 mM methotrexate solution in assay buffer were added to each cuvette to give a methotrexate substrate concentration of 0.06 mM (60 μM). The range of the concentration of CP014 in the cuvettes was 0-400 μM.

The substrate solutions in the cuvettes were heated to 37° C. in an oven. The cuvettes were then placed in turn in a spectrophotometer which was maintained at 37° C. using a Peltier. The assays were commenced by adding a 10 μL aliquot of fusion protein (ScFV anti CEA-CPG2) solution or CPG2 solution, followed by brief stirring. The hydrolysis of the methotrexate substrate was monitored by measuring the decrease in absorbance at 320 nm.

One unit (1 U) of CPG2 activity is defined as the amount of enzyme which catalyses the hydrolysis of 1 μmol of methotrexate per minute at 37° C. The molar extinction coefficient of Scheme 5: (i) Acetyl deprotection conditions: 1 M NaOMe, MeOH, rt, 1 h

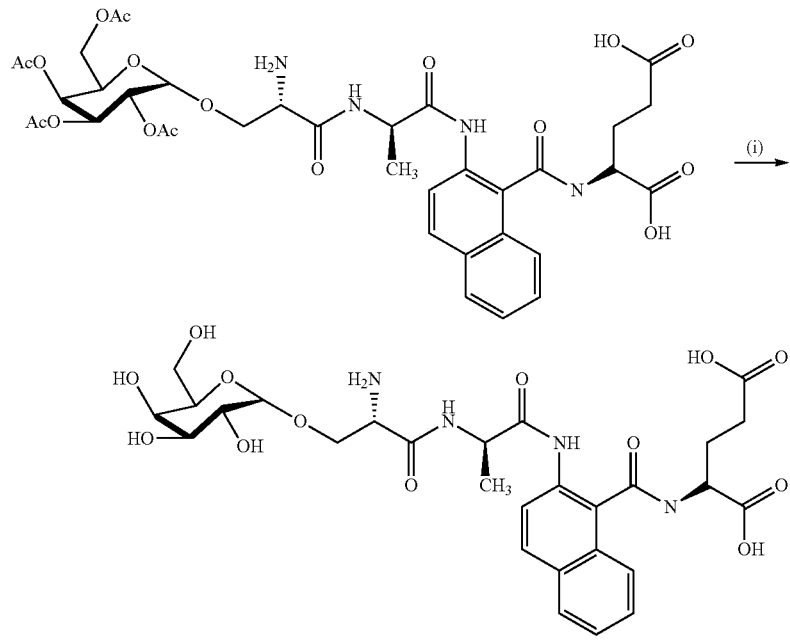

Analytical Methods Used and Data:

The following HPLC traces were obtained for peptide CP014 (FIGS. 1 and 2). Standard reverse phase conditions were employed using an Onyx C18 column and applying a 12-minute elution gradient of 5 to 100% MeCN (0.1% TFA). Elution gradient: Initial 5% MeCN (0.1% TFA) then 100% MeCN (0.1% TFA) at 8-minutes for 1.5 minutes then back to 5% MeCN (0.1% TFA) to the end.

The structure of CP014 was confirmed using LCMS electrospray (ESI) m/z (ESI) 637 (M+H+, 25%). The results are shown in FIG. 3.

Enzyme Inhibition Experiments, with Calculation of IC50
Enzyme Inhibition Assay Method Used for the Assessment of CP014 as an Inhibitor of CPG2 Activity The effect that CP014 had on CPG2 activity was measured using a spectrophotometric assay. CP014 was dissolved in assay buffer (0.1 M Tris-HCl buffer at pH 7.3 containing 0.2 mM zinc chloride) to give a concentration of 40 mM. Various methotrexate was taken as 8300 L mol$^{-1}$ cm$^{-1}$. For each assay a plot of absorbance versus time was created and a straight line was fitted to the data between 0 and 0.2 minutes. The slope of the straight line was then multiplied by minus 12 and the dilution factor of the ScFV anti CEA-CPG2/CPG2 solution to give the enzyme activity in U/mL.

A variation of the assay was to incubate various amounts of CP014 with ScFV anti CEA-CPG2 or CPG for a period of time at 4° C. prior to CPG2 assay. Following this incubation step, a 10 μL aliquot of each mixture was added to a cuvette that contained a 1 mL aliquot of 0.06 mM methotrexate in assay buffer at 37° C. After stirring the contents of the cuvette, the measurement of the decrease in absorbance and subsequent determination of enzyme activity were carried out as described above.

The effectiveness of CP014 in inhibiting CPG2 activity was expressed in terms of its IC$_{50}$ value, i.e. the half maximal inhibitory concentration. Using GraphPad Prism 5 software, the $IC_{50}$ value was determined by applying non-linear regression to a plot of enzyme activity versus the logarithm of the CP014 concentration.

Non-Amplified Amplex Red Assay for the Screening of Potential CPG2 Substrates

It was established that CP014 is a potential inhibitor of CPG2 activity using a spectrophotometric assay. In order to confirm that the material was an inhibitor and not a substrate for the enzyme, a modified version of an assay developed by Invitrogen Inc. was carried out. The so-called Amplex Red assay can be used to measure to measure L-glutamate in food samples and continuously monitor glutamate oxidase activity. By eliminating an amplification step in the assay procedure, it was possible to screen compounds as substrates for CPG2. In the modified assay, L-glutamic acid that has been cleaved from a substrate of CPG2 is oxidised by glutamate oxidase to produce α-ketoglutarate, ammonia and hydrogen peroxide. The hydrogen peroxide then reacts with 10-acetyl-3,7-dihydroxyphenoxazine (Amplex Red reagent) in a 1:1 stoichiometry in a reaction catalysed by horseradish peroxidise (HRP) to generate the highly fluorescent product, resorufin.

25 µM and 200 µM solutions of CP014 in assay buffer (0.1 M Tris-HCl buffer at pH 7.5 containing 0.2 mM zinc chloride), and a 25 µM solution of folic acid in assay buffer were prepared. The Amplex Red reagent mixture was prepared by combining 2.5 µL 10 mM solution of Amplex Red reagent in DMSO, 5 µL HRP solution in assay buffer (100 U/mL), 32 µL L-glutamate oxidase solution in assay buffer (5 U/mL) and 460.5 µL assay buffer solution. ScFV anti CEA-CPG2 fusion protein was diluted appropriately using assay buffer.

A 50 µL aliquot of CP014 solution or 25 µM folic acid solution and a 50 µL aliquot of the Amplex Red reagent mixture were added to a well of a black microtitre plate. The plate was covered, then incubated at 37° C. for 10 minutes. The cover was removed and a 1 µL aliquot of ScFV anti CEA-CPG2 was added. After brief stirring, the plate was placed in a BMG Fluostar Omega plate reader and the fluorescence intensity was monitored over a 245 second period at 5 second intervals. The excitation filter wavelength was set at 544 nm and the emission filter wavelength was set at 590 nm. If a material is a substrate for CPG2, such as folic acid, a plot of fluorescence intensity versus time (in seconds) displays a linear relationship after an initial lag phase. The slope of the straight line portion of the plot has been shown to be directly proportional to CPG2 activity.

When ScFV anti CEA-CPG2 was diluted to a concentration of approximately 2 U/mL, the slope value that was calculated for the 12.5 µM folic acid control assay was approximately 4.0. At concentrations of both 12.5 and 100 µM in the plate well, CP014 yielded slope values that were no greater than that of the negative control sample (i.e. where assay buffer was added to the well rather than ScFV anti CEA-CPG2 solution), indicating that the material was not a substrate for CPG2.

Evaluation of IC50 and Substrate Potential for CP014

Figure 4:
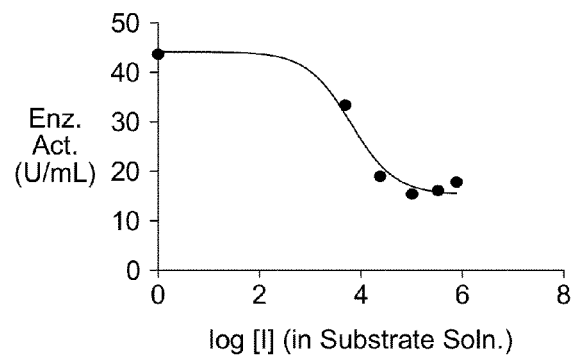
FIG. 4: Inhibition of the CPG2 enzyme activity of ScFV anti CEA-CPG2 by CP014 showing CP014 is an inhibitor of ScFV anti CEA-CPG2. The calculated IC50 is 110 µM.

The IC50 was determined as previously described and the data reduced using Graph pad prism as shown in FIG. 4. The amplex red assay data illustrating substrate potential are shown in FIG. 5.

Figure 5:
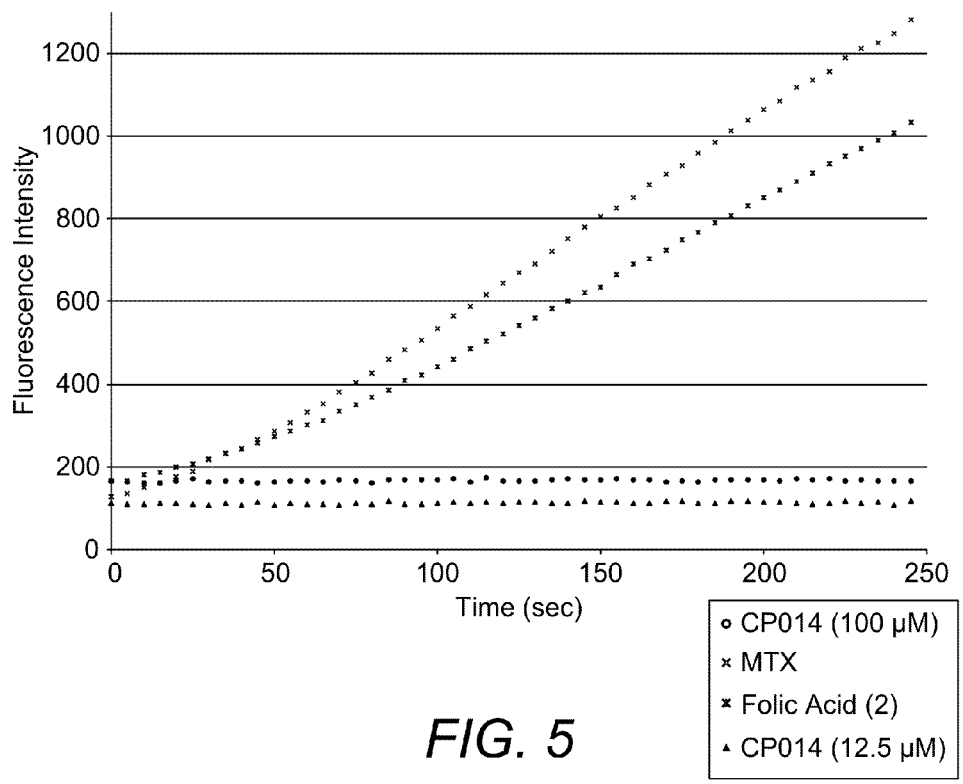
FIG. 5: Results of amplex red assay showing CP014 is not turned over by ScFV anti CEA-CPG2. Substrates Folic acid and methotrexate in the amplex red assay are shown as positive controls. The absence of fluorescence signal with the CP014 demonstrates that CPG2 is not able to use it as a substrate.

The data demonstrates that CP014 inhibits CPG2 activity (FIG. 4) and moreover it is not altered or used as a substrate (FIG. 5).

Binding Studies Using Surface Plasmon Resonance (SPR)

Peptides were coupled to a CM5 chip using EDC/NHS chemistry as recommended by the manufacturer (GE healthcare). Analytes were made up in HBS-P buffer (0.01 M HEPES pH 7.4, 0.15 M NaCl, 0.005% v/v Surfactant P20) and injected over the surface for 180 seconds at 5 µl/min followed by a dissociation time of 300 seconds. Residual binding was removed using two 10 second injections of regeneration buffer (10 mM CHAPS, 1 mM Guanidinium hydrochloride, 2 M NaCl). Response signals and baselines were checked for consistency throughout the experiment and flow rates of 15 and 75 µl/min were tested to confirm minimal effects due to mass transport.

Figure 6A:
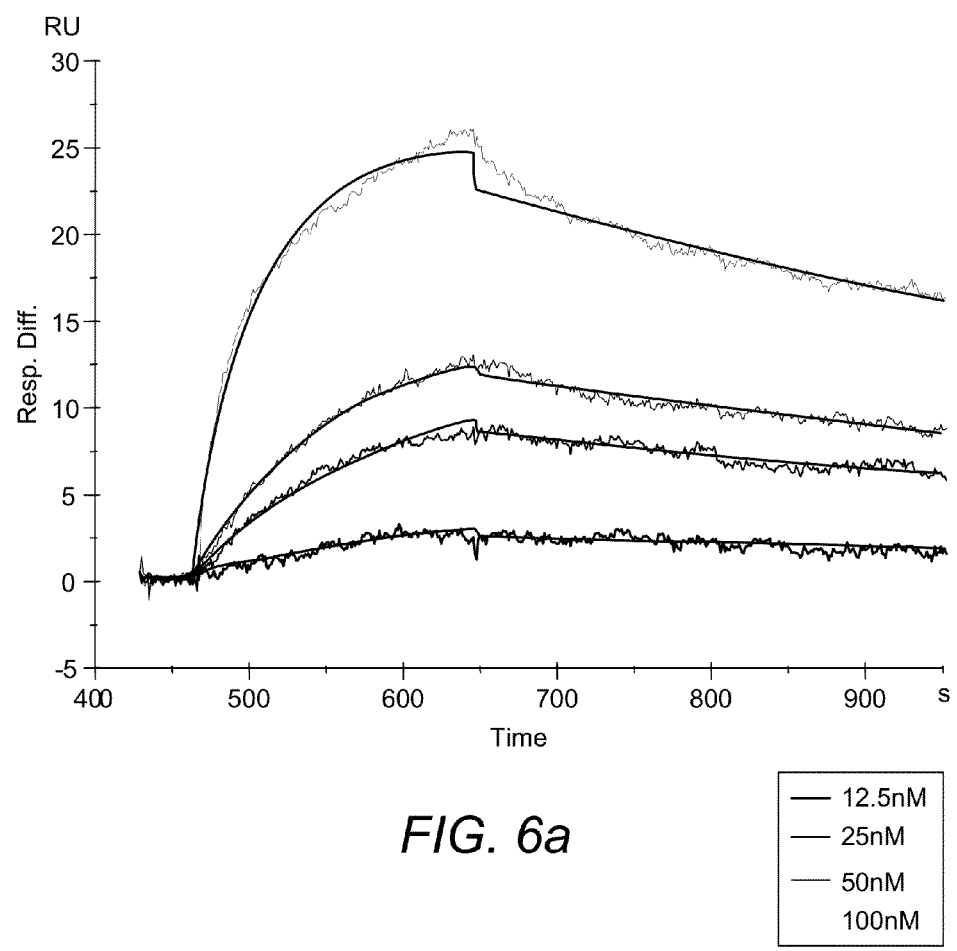
FIG. 6a: Biacore data showing interaction of CP014 and ScFv anti CEA-CPG2 fusion protein applying a 1:1 Langmuir binding model.
Figure 6B:
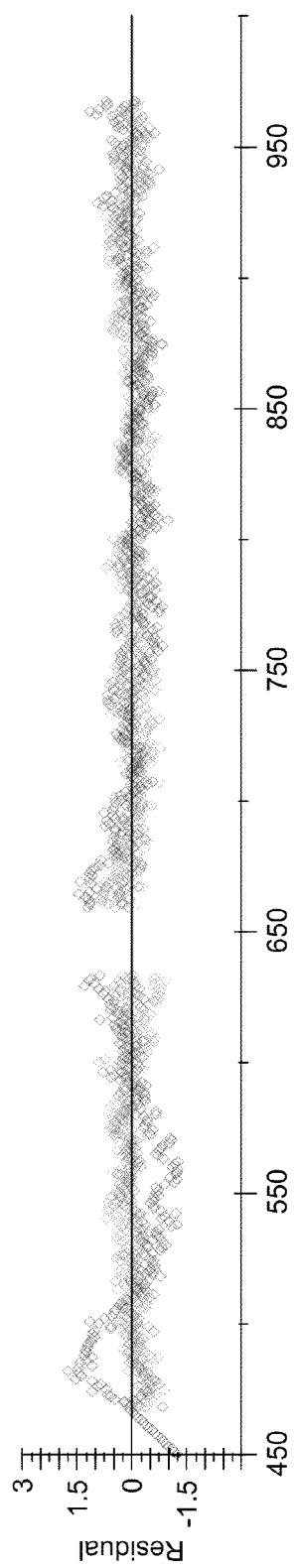
FIG. 6b: Residuals plot showing fit of Biacore data to 1:1 Langmuir binding model.
Figure 6C:
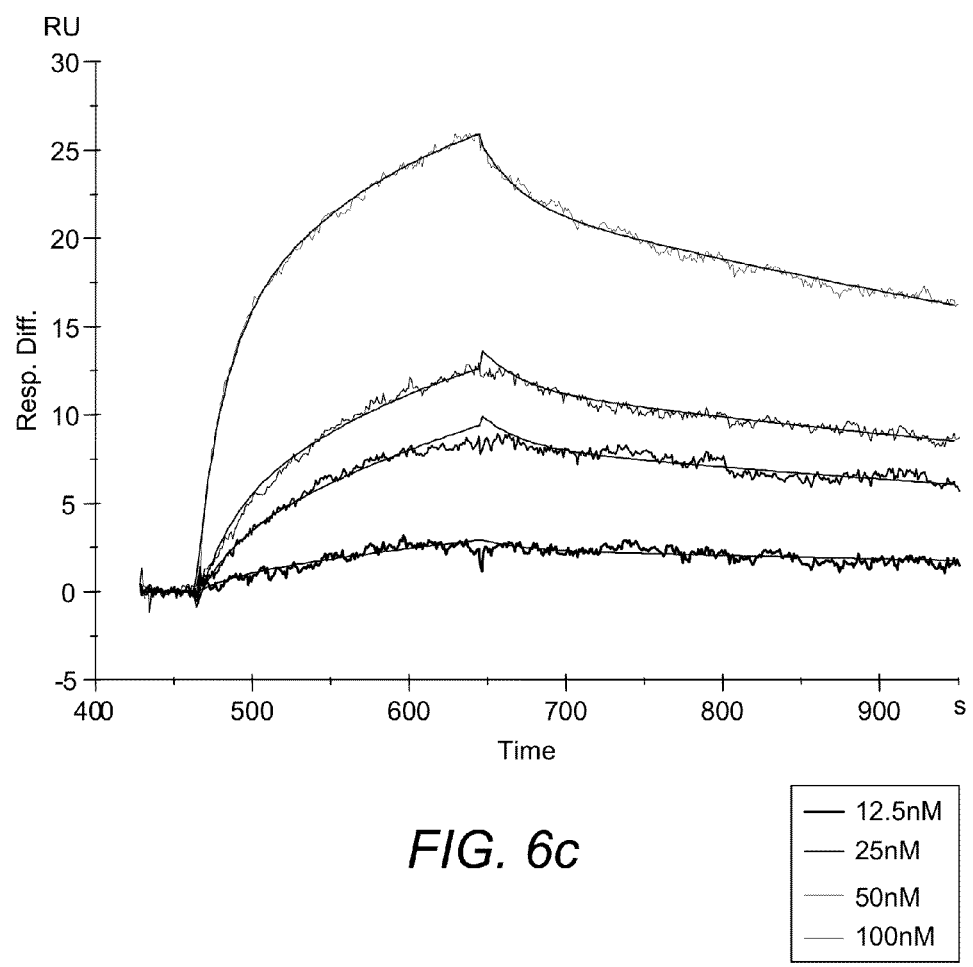
FIG. 6c: Biacore data showing interaction of CP014 and ScFv anti CEA-CPG2 fusion protein applying a 2 state reaction fit.
Figure 6D:
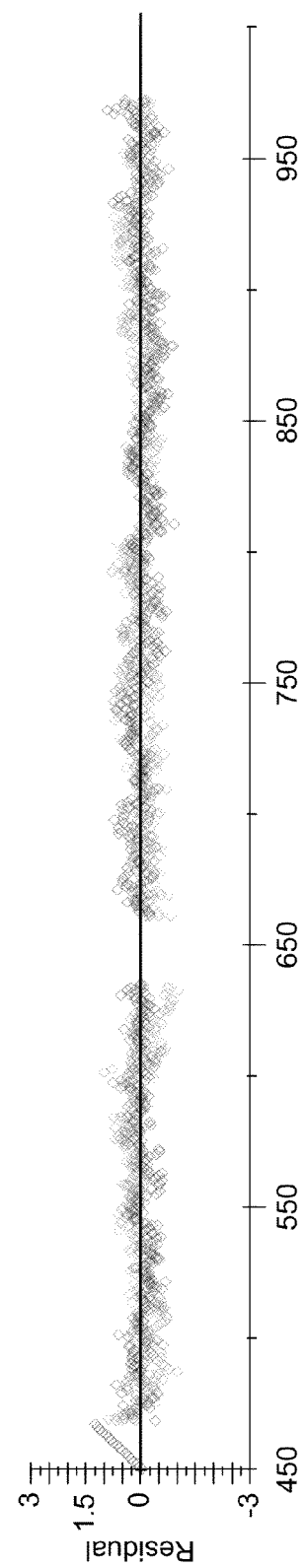
FIG. 6d: Residuals plot showing fit of Biacore data to 2 state binding model.
Figure 7:
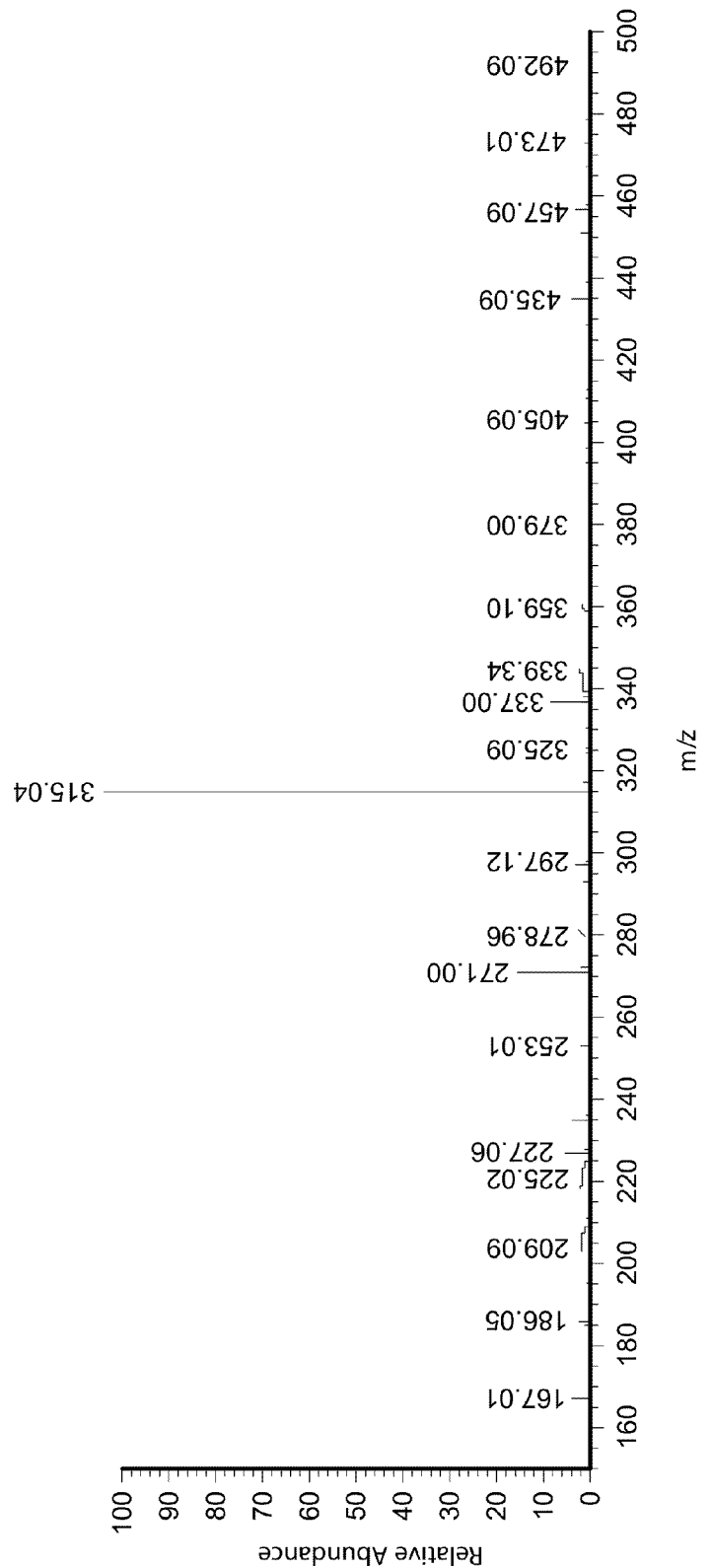
FIG. 7: Electrospray Mass Spectrum of CP006 showing major molecular weight peaks.
Figure 8:
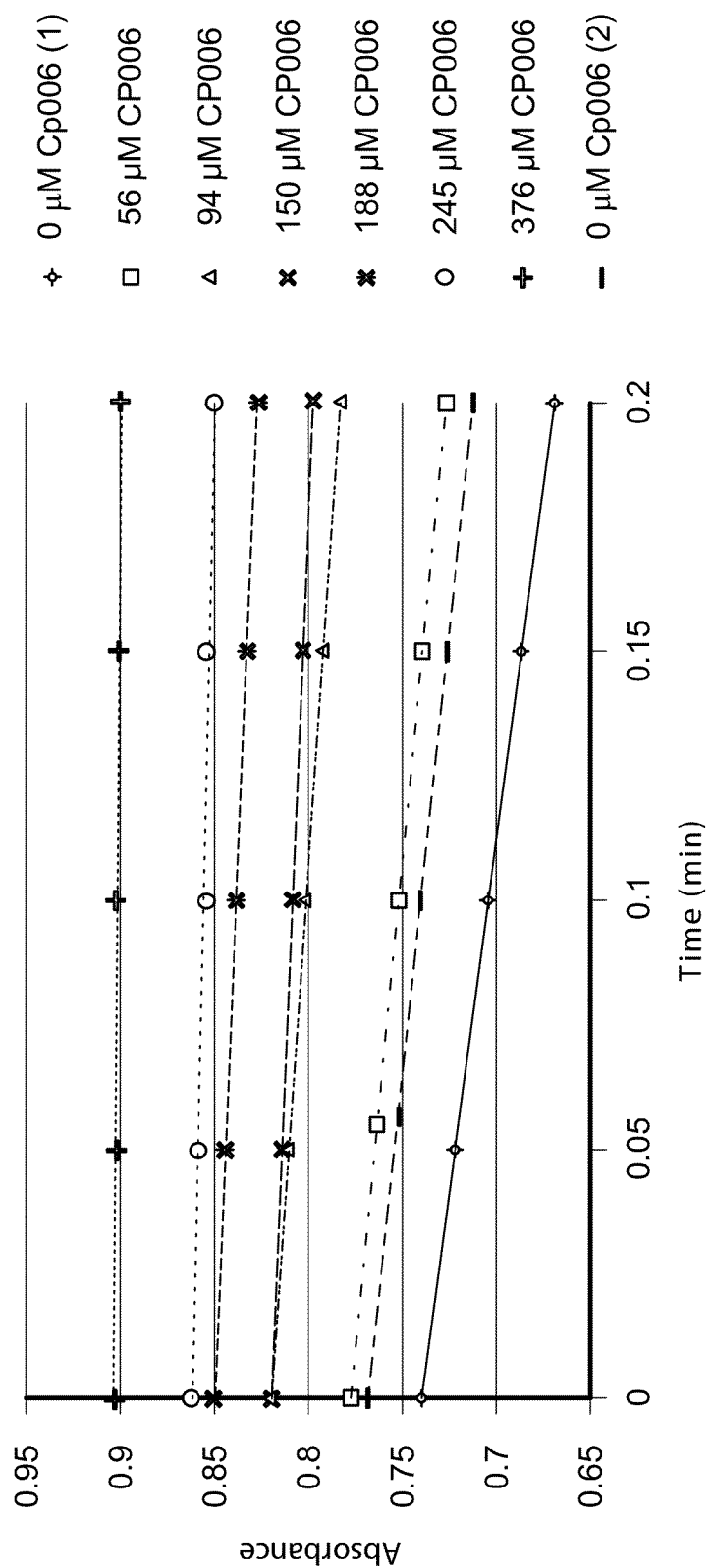
FIG. 8: Inhibition of ScFv anti CEA-CPG2 fusion by CP006 in an inhibition assay. Raw spectral data

FIGS. 6a and 6c each show four sensorgrams overlaid. These are the blank-subtracted real time responses from injections of 12.5, 25, 50 and 100 nM ScFVanti-CEA-CPG2 over the chip surface of immobilised CP014 peptide. The data has been fitted using two different algorithms supplied in the BiaCore software ("Biaevaluation"). The first, shown in FIG. 6a, was a 1:1 binding model (Langmuir) and the second, shown in FIG. 6c, was a 2-state reaction fit. Both fits align closely to the normalised sensorgrams. This can be seen from the residuals plot which shows minimal deviation from the expected values (FIGS. 6b and 6d respectively). In addition, the Chi2 values are 0.154 and 0.0882 respectively and are within the acceptable range (<0.2) for these types of calculation. For both fits the dissociation constant (binding constant KD) was in close agreement at 5 nM and 9 nM, respectively.

The derived kinetic and affinity parameters are summarised in tables 1 and 2 respectively:

TABLE 1

| 1:1 Langmuir fit | | | | |
|---|---|---|---|---|
| Ka (1/Ms) | Kd (1/s) | KA (1/M) | KD (M) | Chi$^2$ |
| 2.26e5 | 1.14e−3 | 1.98e8 | 5.04e−9 | 0.154 |

TABLE 2

| 2 state reaction fit | | | | | |
|---|---|---|---|---|---|
| ka1 (1/Ms) | kd1 (1/s) | ka2 (1/s) | kd2 (1/s) | K (1/M) | Chi$^2$ |
| 2.84e5 | 0.0258 | 0.014 | 1.58e−3 | 1.09e8 | 0.0882 |

Note
the unit for the ka2 value in the 2-state model is per seconds (s$^{-1}$), as displayed by the Biaevaluation software.

Example 3

Clearing Agent Enzyme Binder CP006

Chemical Description and Graphical Representation of the Compound Designated CP006

CP006 is the forerunner to CP014 and its synthesis and structure are described below.

Formula I

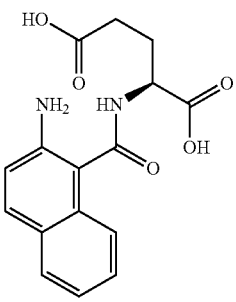

CP006: ANA-Glu-OH where ANA is amino-naphthoic acid

Synthesis of CP006

IIDQ resin (500 mg, 1.91 mmol/g) was rinsed and swollen in 10 ml acetonitrile for one hour and the solvent drained under vacuum. Then Boc-amino naphthoic acid (polypeptide, 100 mg, 0.35 mmol) and H-Glu(OtBu)-OtBu (Bachem, 108 mg, 0.37 mmol) were dissolved in 5 ml acetonitrile and added to the preswollen resin and stirred gently for 72 hours at RT. The reaction was drained into a clean flask and solvent removed in vacuo. To the residue 50 ml of 50% TFA/DCM was added and stirred vigorously for 2 hours. After removal of solvent the residue was rinsed in ice cold tertbutyl methyl ether twice and decanted to leave a yellow solid. Dried crude material was redissolved in 5% acetonitrile (0.1% TFA) and purified by HPLC using an increasing gradient of 5-100% acetonitrile 0.1% TFA. Pooled fractions were reduced in vacuo, diluted in 50% acetonitrile and further freeze dried to afford a white powder. ESMS-ve expected mass: 316.11, measured mass 316.04. Methods for the evaluation of enzyme inhibition and utility as a substrate for CPG2 were tested using the method previously described.

CP006 is an inhibitor of CPG2 activity in scFv Anti CEA-CPG2 and is a Poor Substrate.

Figure 9:
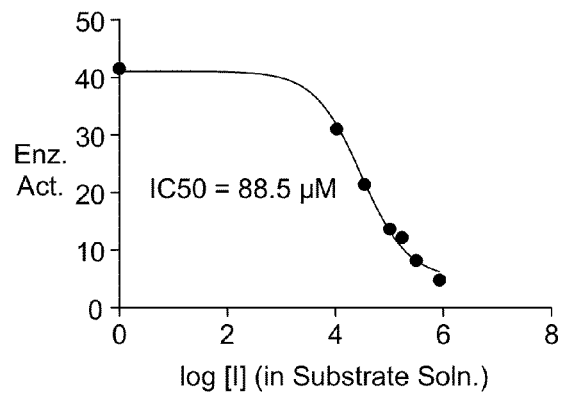
FIG. 9: Inhibition of ScFv anti CEA-CPG2 fusion by CP006 in an inhibition assay. Inhibition curve showing an IC50 of 88.5 µM.
Figure 10:
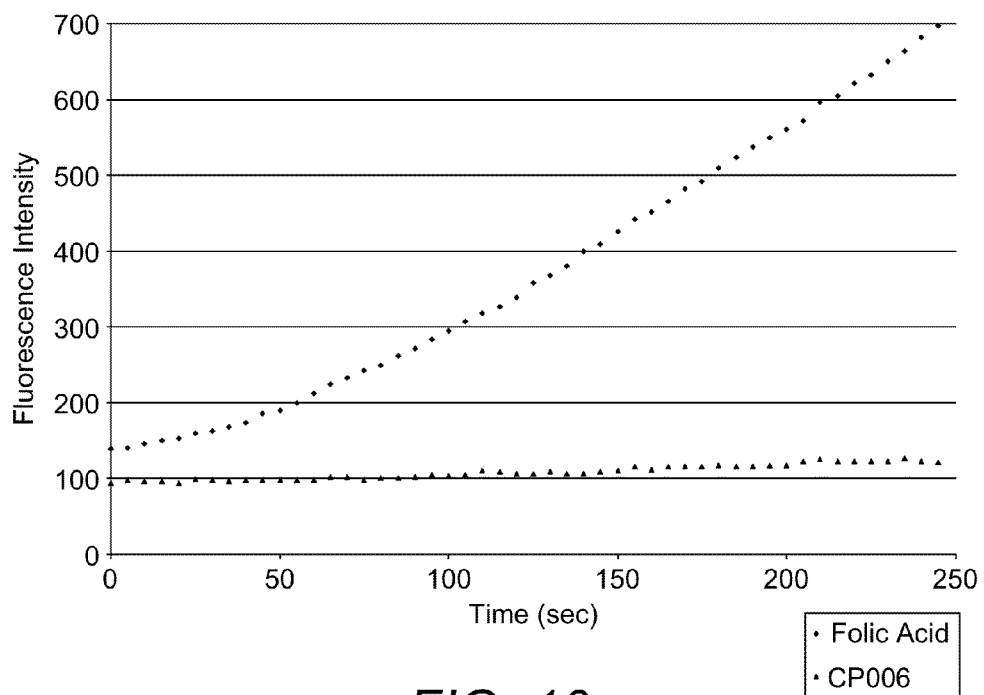
FIG. 10: Amplex red assay results showing low substrate activity for CP006 and MFECP. The substrate concentration was 12.5 µM.

The IC50 was determined as previously described and the data reduced using Graph pad prism as shown in FIG. 9. The amplex red assay data illustrating substrate potential are shown in FIG. 10.

Example 4

Cell Binding Studies with Sheep Anti CEA and scFv Anti CEA-CPG2 Fusion Protein

A study to look at antibodies generated in sheep to CEA and the ScFv anti CEA-CPG2 Fusion protein was carried out with analysis using flow cytometry.
Measurement by Flow Cytometry of Binding Capability of scFv Anti-CEA-CPG2 Using CEA Expressing Cells.
Materials:
Cells Lines:
CRL 1573—control cell line, CCL 229 (LoVo)—CEA expressing cell line
Antibodies/Conjugates:
CPG2-PE (Phycoerythrin), CPG2 100 U/ml 1:100 dilution of 100 U conjugated
ScFv anti-CEA-CPG2-PE UCL, 40-50 U/ml, 0.71 mg/ml protein 2.5 µg/ml in buffer containing BSA
Sheep anti-CEA-PE, CF 1110-PE; Stock at 670 µg/ml.
Mouse anti human CEA UCL at 3.9 mg/ml 2.5 µg/ml in buffer containing BSA
Goat anti-Mouse-PE Southern Biotech 1050-09 L2806-XH69Z kappa chain specific at 0.25 mg/ml used at 1 µg/ml
4.5 ml polystyrene tubes, PBS azide, BSA, PBS+0.5% Formaldehyde (Polysciences #18814), Propidium Iodine (Orpegen at 100 mg/ml)
Centrifuge Eppendorf 5810R set to 250G, 5 mins, 4° C.
Coulter XL flow cytometer
Method:
Cultured cells were both used at $2\times10^5$ cells per tube, cells in tubes were prepared to contain the following
1. Nothing added, auto fluorescence tested
2. Propidium Iodine at a final concentration of 10 µg/ml
3. CPG2-PE
4. ScFv anti CEA-CPG2-PE
5. Sheep anti CEA-PE
6. Mouse anti CEA/anti Mouse-PE Cells were spun down and 100 µl of antibody solution was added to respective tube. 100 µl buffer was added to tubes 1 and 2 and left in fridge until later.

Tubes were incubated in the dark at 4° C. for 1 hour, add 1 ml $PBS_{AB}$ and spun as above. Include tube 1 in this wash. The supernatant was removed and 100 µl conjugate was added to tube 6 for a further incubation of 1 hr in the dark at 4° C.

Added 150 µl 0.5% formaldehyde to tubes 1, 3, 4 and 5, stored in the fridge until measured (~2 hours). Washed tube 6 as before and add formaldehyde to this tube. 30 minutes before measuring add 100 µl Propidium Iodine to tube 2, before measuring, added 1 ml of PBS to all samples.

Figures 11E, 11F:
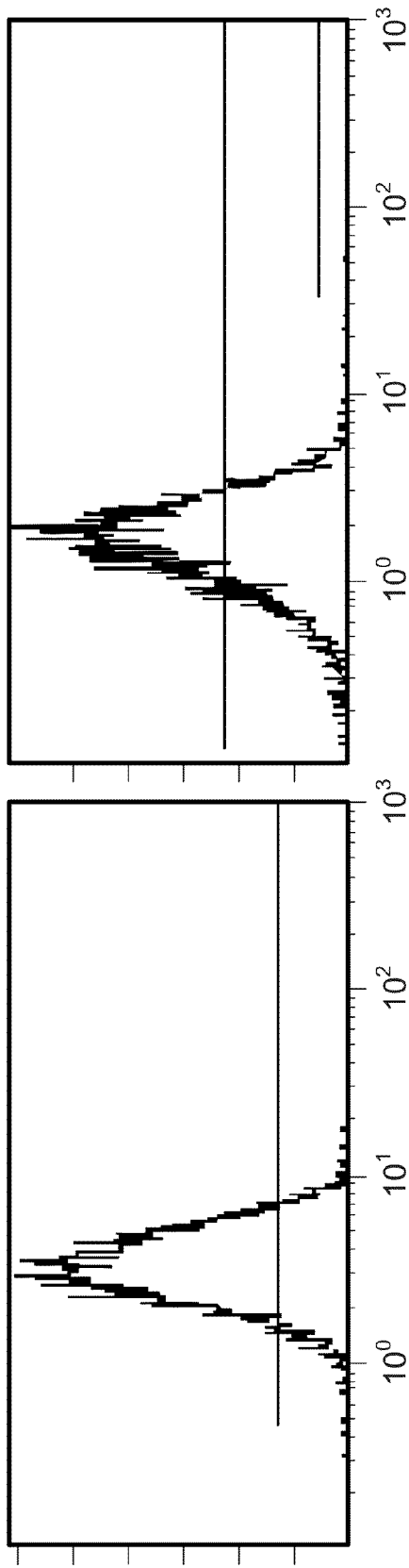
FIG. 11e/f shows flow cytometry results for a control against ssFV anti-CEA-CP-PE binding with a control (CEA surface antigen negative) cell line (CRL 1573).

The control cell line shows no specific binding of any anti-CEA antibody (FIG. 11a to j). There is a slight non specific binding of the sheep antibody (FIG. 11h). The first picture in each of FIGS. 11a to 11j (i.e. FIGS. 11a, 11c, 11e, 11g and 11i) is a control that should not show any difference between the samples.

Figure 12D:
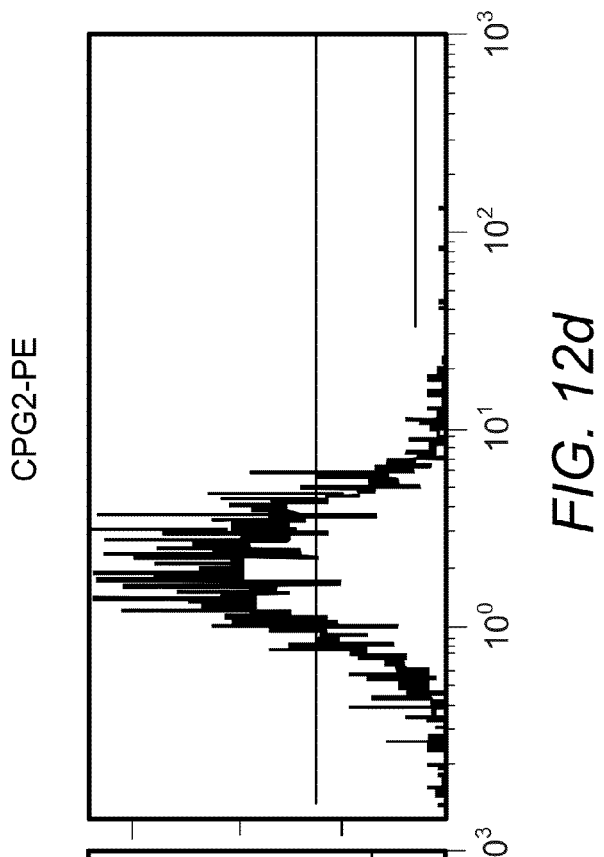
FIG. 12a/b shows flow cytometry results of a control against auto-fluorescence with a CEA surface antigen positive cell line (CCI-229).
FIG. 12c/d shows flow cytometry results for a control against CPG2-PE binding with a CEA surface antigen positive cell line (CCI-229).
FIG. 12e/f shows flow cytometry results for a control against ssFV anti-CEA-CP-PE binding with a CEA surface antigen positive cell line (CCI-229).
FIG. 12g/h shows flow cytometry results for a control against sheep anti-CEA-PE binding with a CEA surface antigen positive cell line (CCI-229).
FIG. 12i/j shows flow cytometry results for a control against A5B5 anti-CEA+goat anti-mouse-PE binding with a CEA surface antigen positive cell line (CCI-229).
Figure 12C:
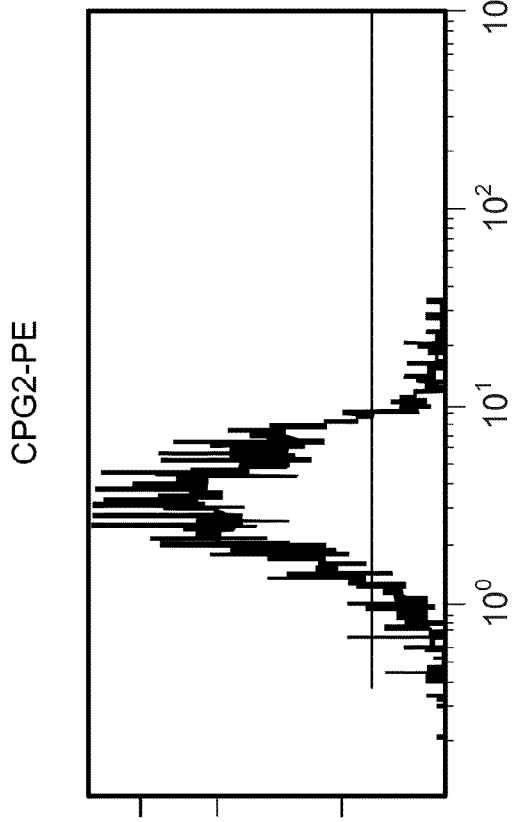
Figures 12G, 12H:
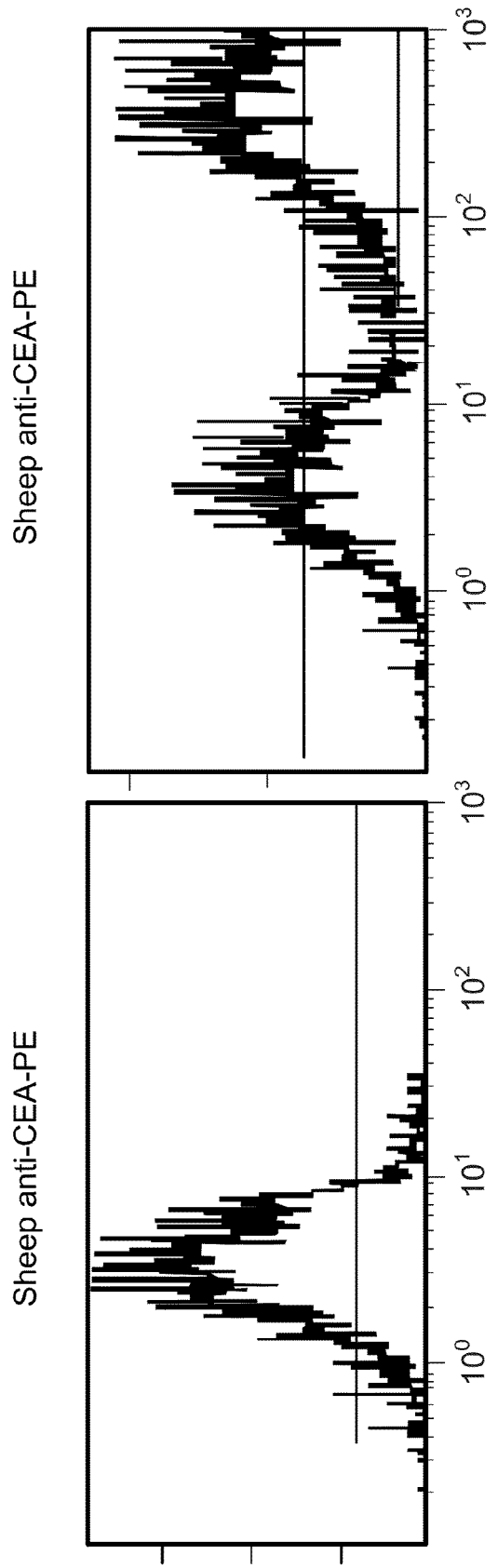

CCL 229 cells show slightly more auto-fluorescence compare to the negative control cell line (FIG. 12b). The CPG2 control does not bind to the cell line (FIG. 12d), however there are 2 populations of cells amongst the CEA expressing cell line, one that presents the surface protein CEA and one that does not. This phenomenon is shown with all three anti-CEA antibody combinations (FIGS. 12f, 12h and 12j).

REFERENCES

1) M. P. Napier, S. K. Sharma, C. J. Springer, K. D. Bagshawe, A. J. Green, J. Martin, S. M. Stribbling, N. Cushen, D. O'Malley, and R. H. J. Begent Antibody-directed Enzyme Prodrug Therapy: Efficacy and Mechanism of Action in Colorectal Carcinoma. Clinical Cancer Research 2000, 6: 765-772. (Refers to the prior art antibody clearing agent)
2) Geysen H M, Meloen R H, Barteling S J. Use of peptide synthesis to probe viral antigens for epitopes to a resolution of a single amino acid. Proceedings of the National Academy of Sciences USA 1984, 81: 3998-4002.
3) Meloen R H, Puijk W C, Schaaper W M M. Epitope mapping by PEPSCAN. In: Immunology Methods Manual. Ed Iwan Lefkovits 1997, Academic Press, pp 982-988.
4) Connors T A and Knox R J. Stem Cells 1995; 13:501-511.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A peptide clearing agent for clearance of a conjugate of
   a. an enzyme; and
   b. a binding molecule which binds specifically at a target location,
from a non-target location in a subject comprising a first domain which binds to the active site of the enzyme and a second domain, which binds to the asialoglycoprotein receptor expressed by hepatic cells to facilitate clearance of the conjugate, bound via the first domain, through the liver wherein the peptide is no more than 30 amino acids in length and comprises the dipeptide amino-naphtoic (ANA)-glutamate (Glu).

2. The peptide of claim 1 wherein the peptide is glycosylated to facilitate clearance through the liver by binding to hepatic cells expressing an asialoglycoprotein receptor.

3. The peptide according to claim 1 wherein the peptide prevents or inhibits enzyme activity upon binding to the enzyme.

4. The peptide according to claim 1 wherein the peptide is not modified by the enzyme activity.

5. The peptide according to claim 1 which comprises the amino acid sequence serine (Ser)-Alanine (Ala)-amino-naphthoic acid (ANA)-glutamate (Glu) (SEQ ID NO: 1).

6. The peptide of claim 5 wherein the serine residue is glycosylated.

7. The peptide according to claim 1 wherein the enzyme is concentrated at a target location through specific binding of the binding molecule at the target location.

8. The peptide according to claim 1 wherein the binding molecule is an antibody or antigen-binding derivative thereof.

9. The peptide according to claim 1 wherein the enzyme acts to convert a pro-drug to an active drug at the target location.

10. The peptide according to claim 1 wherein the peptide has an affinity for the enzyme that is sufficient to permit clearance of the enzyme from the non-target location.

11. The peptide according to claim 1 wherein the peptide has a sufficiently rapid dissociation rate or high dissociation constant to not significantly affect enzyme activity at the target location.

12. The peptide according to claim 1 wherein the peptide's affinity for the enzyme is around 10 fold lower than the binding affinity of the binding molecule for its target location.

13. The peptide according to claim 1 wherein the target location is an antigen expressed by tumour cells.

14. The peptide according to claim 2 wherein the glycosylation involves coupling of one or more galactose groups.

15. The peptide according to claim 1 wherein the peptide is no more than 10 amino acids in length.

16. The peptide according to claim 1 wherein the peptide is minimally immunogenic.

17. The peptide according to claim 1 wherein the peptide is chemically synthesized.

18. The peptide according to claim 1 wherein the enzyme is non-human in origin.

19. The peptide according to claim 1 wherein the enzyme is selected from carboxypeptidase G2, alkaline phosphatase, beta-glucoronidase, penicillin-V-amidase, beta-lactamase, beta-glucosidase and nitroreductase.

20. The peptide according to claim 19 wherein the enzyme is carboxypeptidase G2 (CPG2).

21. A method of producing a peptide clearing agent according to claim 1 comprising:

a. preparing an array of peptides, preferably based upon a starting peptide which is a structural analogue of the enzyme substrate b. screening the array of peptides for binding affinity for the conjugate of an enzyme and a binding molecule which binds specifically at a target location and selecting those with binding affinity c. optionally modifying the amino acid sequence of the peptides with binding affinity in step b and repeating step b using the modified peptides to test for an improvement in binding affinity d. optionally performing a substitution at each residue of the modified peptides found in step c to have improved binding affinity and repeating step b to determine if any of the substituted peptides have further improved binding affinity e. optionally determining whether the peptide or peptides resulting from step c or d (with improved binding affinity) have the ability to prevent or inhibit enzyme activity f. optionally confirming binding specificity for the enzyme by testing with a range of control proteins from the subject g. testing the peptide or peptides for the ability to bind to the asialoglycoprotein receptor expressed by hepatic cells to facilitate clearance through the liver, wherein steps e and f, if performed, can be carried out in either order and step g can be carried out at any point in the method, including providing an array of peptides in step a capable of binding to the asialoglycoprotein receptor expressed by hepatic cells to facilitate clearance through the liver.

22. The method of claim 21 wherein step g comprises glycosylating the peptide or peptides and thus step a may comprise providing an array of glycosylated peptides.

23. The method according to claim 21 wherein step a is performed using a peptide library.

24. The method according to claim 21 wherein the enzyme is CPG2.

25. The method according to claim 21 wherein the starting peptide is the tripeptide WFE.

26. The method according to claim 21 further comprising comparing the amino acid sequence of the peptide produced by the method with a human amino acid sequence database to confirm the peptide is unlikely to have an undesired biological activity.

27. An antibody directed enzyme pro-drug therapy (ADEPT) method comprising use of a peptide according to claim 1 as a clearing agent.

28. A peptide according to claim 1 for use as a clearing agent in antibody directed enzyme pro-drug therapy (ADEPT).

* * * * *